United States Patent
Hine et al.

(10) Patent No.: US 7,142,919 B2
(45) Date of Patent: Nov. 28, 2006

(54) RECONFIGURABLE, FAULT TOLERANT MULTIPLE-ELECTRODE CARDIAC LEAD SYSTEMS

(75) Inventors: Douglas S. Hine, Forest Lake, MN (US); Ven Manda, Stillwater, MN (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 341 days.

(21) Appl. No.: 10/692,647

(22) Filed: Oct. 24, 2003

(65) Prior Publication Data

US 2005/0090870 A1    Apr. 28, 2005

(51) Int. Cl.
    *A61N 1/18* (2006.01)
(52) U.S. Cl. ........................................ 607/17
(58) Field of Classification Search ........... 600/300; 607/9, 23, 24, 17
    See application file for complete search history.

(56) References Cited

U.S. PATENT DOCUMENTS

| | | | |
|---|---|---|---|
| 5,174,288 A | 12/1992 | Bardy et al. | |
| 5,213,098 A | 5/1993 | Bennett et al. | |
| 5,261,418 A | 11/1993 | Ferek-Petric et al. | |
| 5,265,601 A | 11/1993 | Mehra | |
| 5,454,838 A | 10/1995 | Vallana et al. | |
| 5,540,727 A | 7/1996 | Tockman et al. | |
| 5,549,109 A | 8/1996 | Samson et al. | |
| 5,549,650 A | 8/1996 | Bornzin et al. | |
| 5,628,777 A | 5/1997 | Moberg et al. | |
| 5,682,885 A | 11/1997 | Littmann et al. | |
| 5,693,075 A | 12/1997 | Plicchi et al. | |
| 5,800,465 A | 9/1998 | Thompson et al. | |
| 5,876,353 A | 3/1999 | Riff et al. | |
| 5,957,861 A | 9/1999 | Combs et al. | |
| 5,987,352 A | 11/1999 | Klein et al. | |
| 6,077,236 A | 6/2000 | Cunningham | |
| 6,094,596 A * | 7/2000 | Morgan .................... 607/5 |
| 6,122,553 A | 9/2000 | Ideker et al. | |
| 6,141,594 A | 10/2000 | Flynn et al. | |
| 6,205,357 B1 | 3/2001 | Ideker et al. | |
| 6,212,434 B1 | 4/2001 | Scheiner et al. | |

(Continued)

OTHER PUBLICATIONS

Pinski, S. and Trohman, R. "Interface in Implanted Cardiac Devices, Part II", Journal of Pacing and Clinical Electrophysiology, vol. 25, No. 10, Oct. 2002, 1496-1509.

*Primary Examiner*—George Manuel
*Assistant Examiner*—Lenwood Faulcon, Jr.
(74) *Attorney, Agent, or Firm*—Paul H. McDowall; Girma Wolde-Michael

(57) ABSTRACT

The present invention provides a method and apparatus for assessing ventricular function on a chronic basis using a plurality of electrodes disposed on or about a left ventricle and/or a right ventricle—and optionally, at least one mechanical or metabolic sensor—all operatively electrically coupled to an implantable medical device. The plurality of electrodes are preferably spaced-apart so that at least one electrode is disposed electrical communication with a discrete volume of ventricular tissue. In one embodiment, the discrete volume of tissue is defined by multiple longitudinal and axial planes as known and used in the medical arts. Thus, according to the present invention, at least one electrode couples to appropriate sensing circuitry and essentially provides a localized electrogram (EGM) that, when compared to other EGMs, provides for configurable, localized delivery of therapeutic pacing stimulus, diverse impedance-sensing vectors, various diagnostic information regarding myocardial function and/or anti-tachycardia pacing.

3 Claims, 17 Drawing Sheets

U.S. PATENT DOCUMENTS

| | | |
|---|---|---|
| 6,223,082 B1 | 4/2001 | Bakels et al. |
| 6,278,894 B1 | 8/2001 | Salo et al. |
| 6,321,123 B1 | 11/2001 | Morris et al. |
| 6,473,645 B1 | 10/2002 | Levine |
| 6,512,949 B1 | 1/2003 | Combs et al. |
| 6,567,704 B1 | 5/2003 | Sundquist et al. |
| 6,795,732 B1 * | 9/2004 | Stadler et al. ................ 607/17 |
| 2002/0120318 A1 * | 8/2002 | Kroll et al. ................ 607/149 |
| 2002/0143380 A1 | 10/2002 | Dahl et al. |
| 2003/0023278 A1 | 1/2003 | Pastore et al. |
| 2003/0083702 A1 * | 5/2003 | Stadler et al. ................ 607/14 |
| 2003/0093130 A1 | 5/2003 | Stypulkowski |
| 2004/0049235 A1 | 3/2004 | Deno et al. |

\* cited by examiner

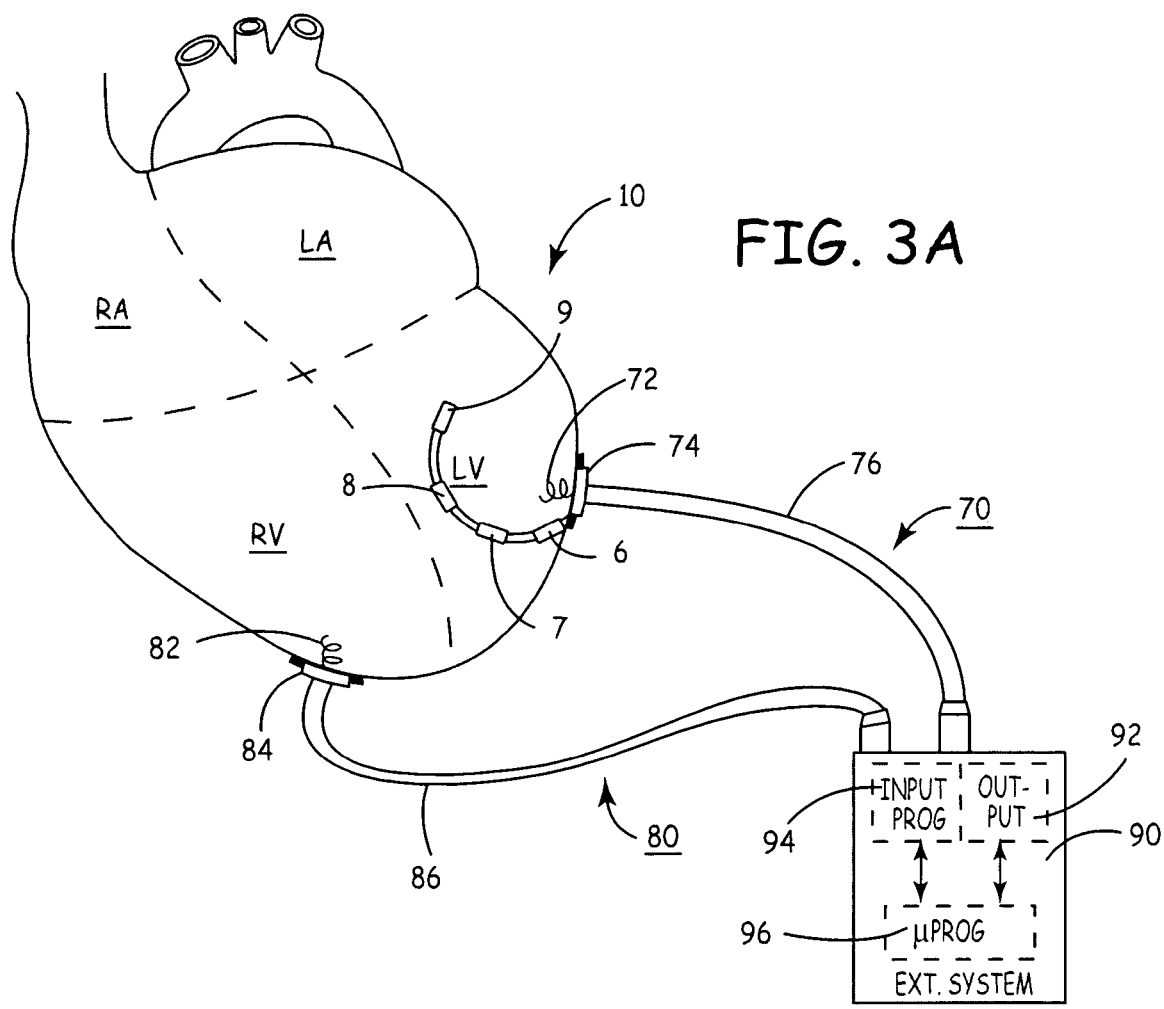

CORONARY ARTERY TERRITORIES
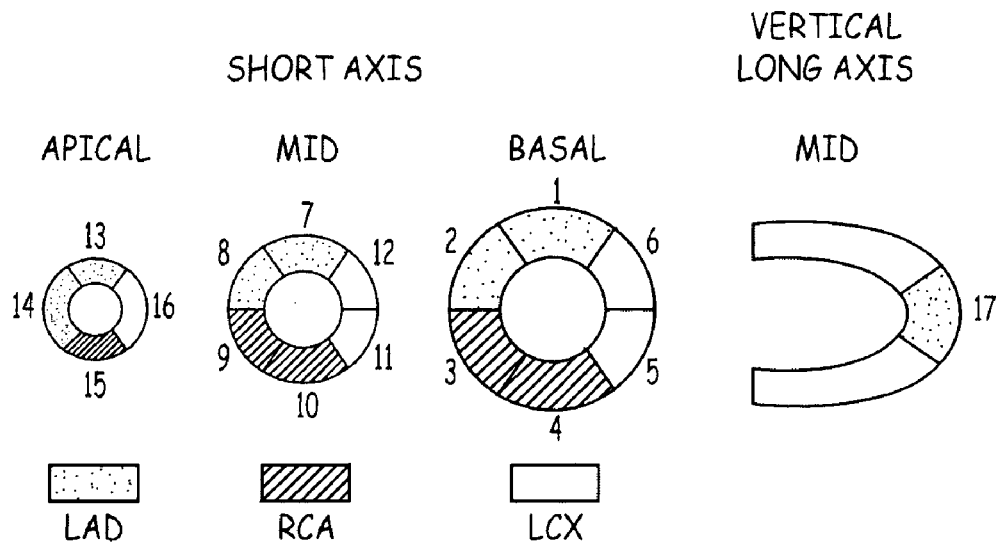
FIG. 3B
LEFT VENTRICULAR SEGMENTATION
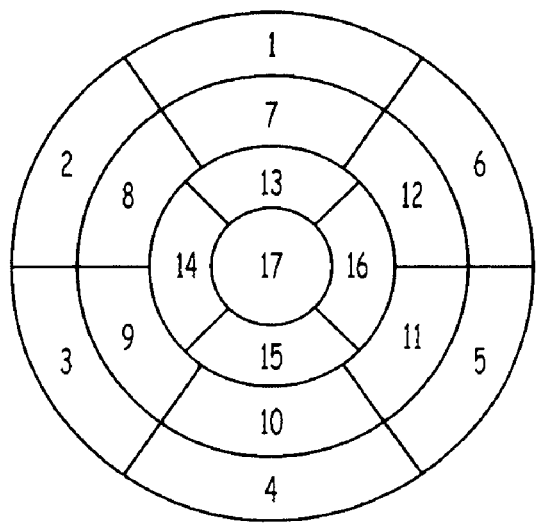
1. basal anterior
2. basal anteroseptal
3. basal inferoseptal
4. basal inferior
5. basal inferolateral
6. basal anterolateral
7. mid anterior
8. mid anteroseptal
9. mid inferoseptal
10. mid inferior
11. mid inferolateral
12. mid anterolateral
13. apical arterior
14. apical septal
15. apical inferior
16. apical lateral
17. apex

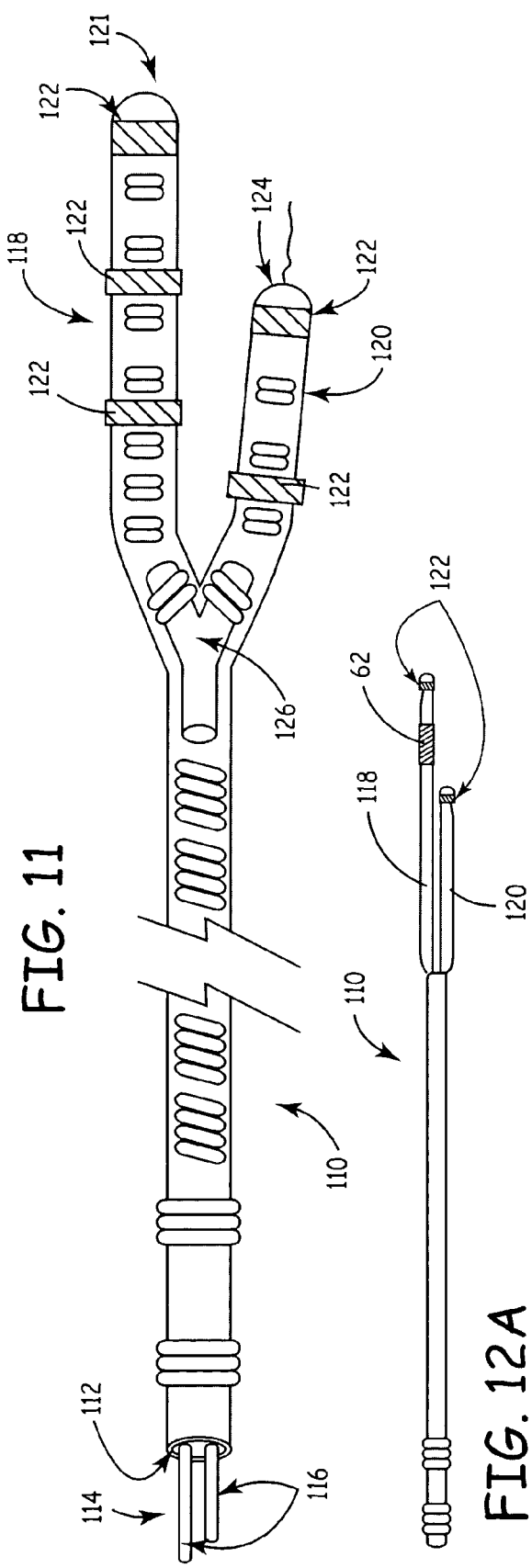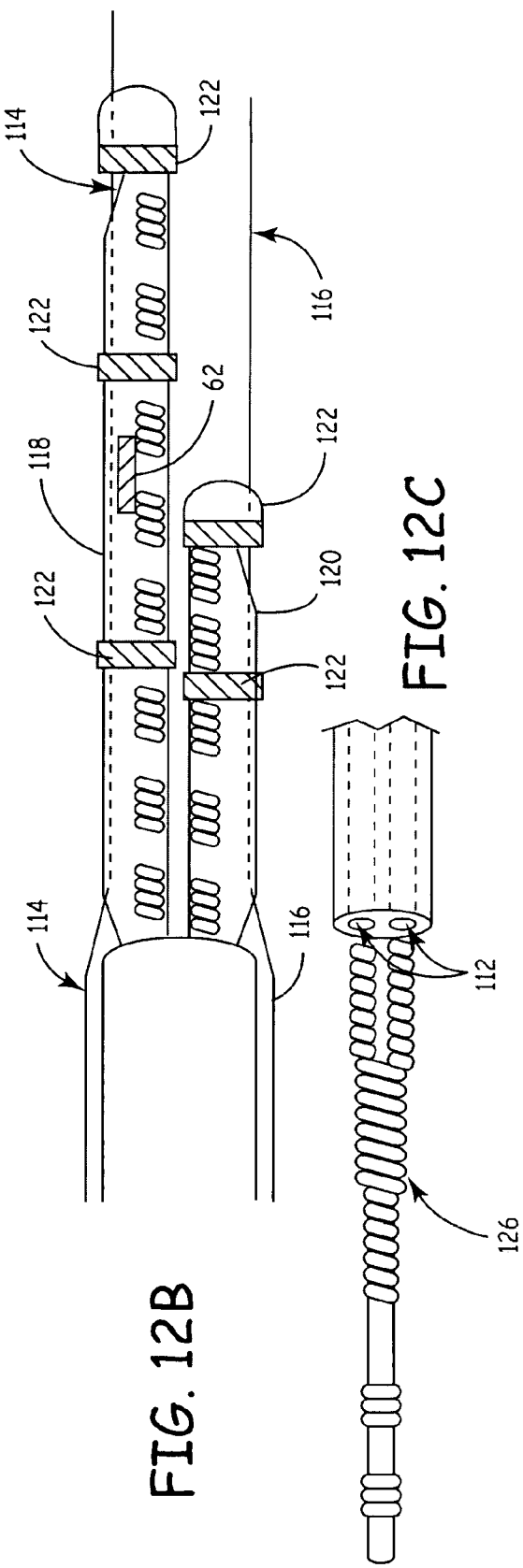

RECONFIGURABLE, FAULT TOLERANT MULTIPLE-ELECTRODE CARDIAC LEAD SYSTEMS

CROSS-REFERENCE TO RELATED APPLICATIONS

This patent application relates to and hereby incorporates by reference the contents of non-provisional U.S. patent application Ser. No. 10/684,759 filed on 14 Oct. 2003 and entitled, "METHOD AND APPARATUS FOR MONITORING TISSUE FLUID CONTENT FOR USE IN AN IMPLANTABLE CARDIAC DEVICE," and non-provisional U.S. patent application Ser. No. 10/680,695 filed 7 Oct. 2003 and entitled, "MULTIPLE PACING OUTPUT CHANNELS."

FIELD OF THE INVENTION

The present invention relates generally to reconfigurable, fault-tolerant medical electrical lead systems for cardiac medical devices. More particularly, the present invention relates to lead systems capable of sensing cardiac events, measuring intrathoracic impedance, and/or delivering diverse electrical stimulation therapies. Optionally, lead systems according to the present invention include mechanical and/or metabolic sensor input to assist in sensing cardiac events (or response to therapy) and optimizing therapy delivery based on an output signal from said sensed events, mechanical and/or metabolic sensor inputs.

BACKGROUND OF THE INVENTION

Left ventricular (LV) function is of interest for both diagnostic and therapeutic applications. During normal cardiac function, the atria and ventricles operate under consistent time-dependent relationships during the systolic (contractile) phase and the diastolic (relaxation) phase of the cardiac cycle. During cardiac dysfunction such as heart failure (HF) or as associated with diverse pathological conditions (e.g., a myocardial infarction, ischemic event, acute decompensation, etc.) or following cardiac-related surgical procedures, these time-dependent mechanical relationships are often altered. In addition, deleterious remodeling of the myocardium (e.g., LV lateral or "free" wall) oftentimes accompanies HF or other pathological conditions of a patient. This alteration and/or remodeling, when combined with the effects of weakened cardiac muscles or modified depolarization patterns, reduces the ability of the LV to generate contractile strength. Given prior art devices and methods, the resulting hemodynamic insufficiency may require clinical intervention.

Ventricular asynchrony following coronary artery bypass graft (CABG) surgery is a problem encountered relatively often, requiring post-operative temporary pacing. Atrio-biventricular pacing has been found to improve post-operative hemodynamics following such procedures. Chronic cardiac resynchronization therapy (CRT) has been clinically demonstrated to improve indices of cardiac function in patients suffering from congestive heart failure and may promote so-called "reverse remodeling." Cardiac pacing may be applied to one or both ventricles or multiple heart chambers, including one or both atria, to improve cardiac chamber coordination, which in turn is thought to improve cardiac output and pumping efficiency. Clinical follow-up of patients undergoing resynchronization therapy has shown improvements in hemodynamic measures of cardiac function, LV volumes, and wall motion. However, not all patients respond favorably to CRT. For example, a patient with a LV myocardial infarct (MI) may have altered dispersion patterns of depolarization, left bundle branch block (LBBB), an ectopic site, and/or a reentry circuit related to the MI. Each of which can negatively affect LV activity, both intrinsic and evoked (e.g., by single-site LV pacing). Physicians are challenged in selecting patients that will benefit and in selecting the optimal pacing locations and pacing intervals applied to resynchronize the heart chamber contractions.

The foregoing physiologic issues can negatively affect the efficacious delivery of diverse cardiac stimulation therapies. Thus, a need exists in the art to overcome some or all or of these physiologic issues in order to maximize safe, efficacious and continuous therapy delivery to a patient.

Selection of atrial-ventricular (A-V) and inter-ventricular (RV-LV) pacing sites and intervals (herein "pacing parameters") oftentimes are based on echocardiographic studies performed to determine the settings resulting in the best acute hemodynamic response. Significant hemodynamic changes may not always be acutely observable in an individual patient, however, using non-invasive monitoring methods. Selection of pacing parameters may therefore be based on avoidance of altered or impeded ventricular filling. In the MIRACLE clinical trial conducted to evaluate CRT, as understood by the inventors, the A-V interval was optimized individually in patients by shortening the A-V interval to maximize ventricular filling without truncating the atrial contribution as observed by echocardiography.

Echocardiographic approaches provide only an open-loop method for optimizing cardiac therapy delivery, such as CRT. After evaluating the hemodynamic effect of varying combinations of pacing parameters, a physician must manually select and program the desired parameters and assume that the patient's device optimal interval settings and electrode location(s) remain unchanged until a subsequent re-optimization visit. Automated systems for selecting timing intervals during multi-chamber pacing have been proposed. A four-chamber pacing system that includes impedance sensing for determining the timing of right heart valve closure or right ventricular (RV) contraction and adjusting the timing of delivery of LV pacing pulses is generally disclosed in U.S. Pat. No. 6,223,082 issued to Bakels et al., incorporated herein by reference in its entirety. Programmable coupling intervals selected so as to provide optimal hemodynamic benefit to the patient in an implantable multichamber cardiac stimulation device are generally disclosed in U.S. Pat. No. 6,473,645 issued to Levine, incorporated herein by reference in its entirety.

In the event that an acute heart failure decompensation event or a spontaneous ventricular tachycardia (VT) occurs, or a patient suffers from an acute MI, cardiac depolarization and repolarization patterns are typically altered. As a result, an electrical therapy that previously produced effective results (e.g., adequate cardiac output, stroke volume and cardiac perfusion) can be rendered ineffective.

Myocardial acceleration during isovolumic contraction derived from tissue Doppler imaging has been investigated as an index of RV activity. Myocardial acceleration was presumed to be constant during the isovolumic contraction. Doppler tissue imaging has also been used to investigate coordination between septal and lateral wall motion for predicting which patients are likely to benefit from CRT. Evidence suggests patient response is dependent on the degree of ventricular synchrony before and after therapy. Doppler tissue imaging studies have shown that the LV mid-lateral to mid-basal segments show the greatest improvement in shortening following CRT. Detection and monitoring of LV activity, therefore, would be useful in optimizing CRT. Myocardial activity is not as preload-dependent or autonomically sensitive as hemodynamic measures of ventricular function. Optimization of CRT based on myocardial activity is expected to be less transient than optimization based on hemodynamic parameters, which could quickly change under autonomic influence or alterations in preload. Myocardial acceleration, however, is not a constant during isovolumic contraction when measured directly by an accelerometer. Therefore, a method is needed for using signals to monitor myocardial acceleration, particularly in the LV for use in assessing cardiac activity and optimizing CRT.

Implantable sensors for monitoring heart wall motion have been described or implemented for use in relation to the RV. A sensor implanted in the heart mass for monitoring heart function by monitoring the momentum or velocity of the heart mass is generally disclosed in U.S. Pat. No. 5,454,838 issued to Vallana et al. A catheter for insertion into the ventricle for monitoring cardiac activity having an acceleration transducer at or proximate the catheter tip is generally disclosed in U.S. Pat. No. 6,077,236 issued to Cunningham. Implantable leads incorporating accelerometer-based cardiac wall motion sensors are generally disclosed in U.S. Pat. No. 5,628,777 issued to Moberg, et al. A device for sensing natural heart acceleration is generally disclosed in U.S. Pat. No. 5,693,075, issued to Plicchi, et al. A system for myocardial tensiometery including a tensiometric element disposed at a location subject to bending due to cardiac contractions is generally disclosed in U.S. Pat. No. 5,261,418 issued to Ferek-Petric et al. All of the above-cited patents are hereby incorporated herein by reference in their entirety.

Detection of peak endocardial wall motion in the apex of the RV for optimizing A-V intervals has been validated clinically. A system and method for using cardiac wall motion sensor signals to provide hemodynamically optimal values for heart rate and AV interval are generally disclosed in U.S. Pat. No. 5,549,650 issued to Bornzin, et al., incorporated herein by reference in its entirety. A cardiac stimulating system designed to automatically optimize both the pacing mode and one or more pacing cycle parameters in a way that results in optimization of a cardiac performance parameter, including for example heart accelerations, is generally disclosed in U.S. Pat. No. 5,540,727, issued to Tockman, et al.

It is apparent from the above discussion that a need remains for providing a device and method for monitoring myocardial activity in the LV and for selecting optimal cardiac pacing intervals that produce the greatest improvement in LV activity during multi-chamber or biventricular pacing delivered to improve heart chamber output and/or intra-chamber synchronization, chronically or acutely. An improved index of LV activity is expected to reflect an improvement in overall cardiac chamber synchrony and function and generally result in a net improvement in cardiac efficiency.

SUMMARY OF THE INVENTION

The present invention provides a method and apparatus for assessing ventricular function on a chronic basis using a plurality of electrodes disposed in electrical communication on or about an LV. Some of the methods and at least one electrode disposed in electrical communication with the RV—and optionally, at least one mechanical or metabolic sensor—all operatively electrically coupled to an implantable pulse generator (IPG). The plurality of electrodes are spaced-apart so that at least a single electrode is disposed in electrical communication with a discrete volume of tissue of the ventricle. In one embodiment, the discrete volume of tissue is described with reference to a long axis view of the LV, said view further divided by planes from one end of the axis to the other, as is known and used in the medical arts (e.g., apical, mid-lateral, lateral, and basal) with each plane further divided into radial segments (e.g., anterior, anteroseptal, inferoseptal, inferior, inferolateral, anterolateral, etc.). Thus, according to the present invention, each electrode couples to appropriate sensing circuitry to provide a localized electrogram (EGM) that, particularly when compared to other local EGMs, yields diagnostic information regarding cardiac function and myocardial activity.

For example, by practicing the methods of the present invention an MI is readily detectable and, as a result, the operative electrodes delivering therapy to or near the region of the MI can be rerouted to effectively deliver therapy elsewhere while avoiding the MI-affected region of the heart.

In addition, the present invention provides a compact and convenient apparatus for performing a localized study of dispersion of depolarization and repolarization wavefronts within cardiac tissue. The velocity and direction of such wavefronts provides valuable information of the topography of conduction of the myocardium. Such information provides direct evidence of conduction anomalies without requiring visual, echocardiographic or tomographic inspection. That is, a clinician need not perform machine vision analysis (including electrophysiology study, echocardiographic examination, SPECT, NMR, MRI or PET scans, fluoroscopy exposure and the like) and accordingly does not need to effectively and physiologically counter conduction anomalies by tailoring therapy delivery based on the current conduction status of a patient. The information inherently incorporates current physiologic parameters reflecting overall autonomic tone of a patient (e.g., regardless of possibly confounding factors such as various cardiac drugs, diet, physical exertion and the like). As a result, an acute episode of cardiac ischemia and/or a (normal) sinus tachycardia due to physical exertion can be identified and, if necessary, rectified.

When delivering customized pacing therapy, the present invention provides a platform for performing what is referred to herein as "cascaded pacing" is used to cause intra-chamber synchronization of depolarization. Thus in the event that a depolarization of one or more volumes of myocardium precedes (or lags) adjacent volumes of myocardium, delivery of pacing stimulation improves hemodynamic performance. In a similar fashion, such cascaded pacing is employed to terminate arrhythmias with an intra-chamber cascade of anti-tachycardia pacing (ATP). In this form of the invention, by decrementing the pacing intervals for at least some of the electrodes during successive cardiac cycles a source of undesirable depolarization wavefronts may be effectively countered. For example, if an ectopic focus or an accessory pathway were initiating conflicting depolarization wavefronts, such cascaded ATP can effectively "peel back" such wavefronts until they diminish or are resynchronized with the desired depolarization timing in a chamber.

The reconfigurable multiple electrode medical electrical lead operated according to certain aspects of the present invention provides fault tolerance (e.g., recording intrinsic and/or paced cardiac activity with electrode pairs not rendered ineffective by an MI) for sensing and/or therapy delivery. In multiple chamber embodiments, other electrode pairs may be used to complement the temporal cardiac information obtained with the multiple electrode lead of the present invention. Electrical communication between the electrodes and operative sense/pace circuitry may be established or changed as is well known in the art. For example, a variety of switching mechanisms may be utilized such as modulator/demodulator circuitry, multiplex circuitry, digital switches, and a variety of logic-based programmable units. A single pair of elongated conductors may couple the circuitry to the electrodes or a plurality of insulated conductors (e.g., braided or woven) and the like may be used.

Moreover, in the event that one or more of the plurality of electrodes is rendered ineffective or inoperable due to disengagement from adjacent myocardial tissue, electrical open or short circuit condition, or non-optimal disposition the affected electrodes are eliminated from therapy delivery circuitry (and/or cardiac activity sensing circuitry). This aspect of the present invention offers a modicum of fault tolerance so that therapy delivery may continue unimpeded, possibly indefinitely.

The present invention may also be employed to non-invasively improve pacing therapy delivery in the event that inadvertent phrenic nerve stimulation occurs during pacing therapy delivery. Stimulation of the phrenic nerve can cause patient discomfort when excitable non-cardiac muscle tissue contracts during pacing therapy delivery. Such stimulation may occur more frequently during therapy delivery to an LV due to the proximity of portions of the phrenic nerve to pacing electrodes disposed within one or more cardiac veins. The phrenic nerve originates in the upper half of the spinal cord, between the third and fifth cervical vertebrae, and extends to innervate the diaphragm muscle. The phrenic nerve is responsible for transmitting nerve impulses to the diaphragm that cause the diaphragm to contract and expand, facilitating breathing. Obviously, inadvertent stimulation of the phrenic nerve can distract or irritate a patient, interrupt respiration and/or cause physical discomfort. According to this form of the present invention a multiple electrode LV pacing sequence is altered under patient and/or clinician observation. In the event that symptoms of inadvertent phrenic stimulation are observed the pacing sequence is altered until the symptoms terminate or at least abate. The pacing sequence used to terminate (or abate) such symptoms is then programmed for chronic pacing therapy delivery. In a clinician- or patient-initiated form of this embodiment, the above-mentioned iterative process automatically occurs within an implantable medical device (IMD) upon receipt of a command. A telemetric command for initiating the process can be delivered from a hand-held device, a programming device for the IMD, and the like. The command may be encrypted or require authentication so that the iterative process only occurs when and where desired. Of course, a clinician may "manually" reprogram the therapy delivery modality to reduce symptoms of phrenic nerve stimulation while observing patient response thereto. Such a manual iterative process requires telemetric interrogation of an IMD to reveal which electrode(s) of a multiple electrode medical lead are operatively delivering therapy and subsequent reprogramming of the operative electrodes (e.g., the number and location of the electrodes employed and the sequence in which the electrodes deliver therapy, etc.). Of course, all of the methods according to the present invention may be stored as executable instructions stored on a computer readable medium.

Optionally, a mechanical or metabolic sensor may be operatively coupled to provide an additional complement of temporal information in sensing physiologic activity of a patient, monitoring a therapy delivery system, and optimizing therapy delivery. In one form of this embodiment, an accelerometer couples to a distal portion of a reconfigurable multiple electrode lead adapted for deployment within the great vein or other cardiac vein(s) of the LV. The output signal from the accelerometer can be used to confirm one or more of the following: loss of capture (due to an Ml or other cause) for a single pacing pulse or coupled pacing pulses (e.g., during extra-systolic stimulation therapy delivery), synchrony (or lack thereof) during delivery of CRT, presence of pulse-less electrical activity (also known as electro-mechanical dissociation or EMD), timing optimization for multi-site pacing therapy in a single chamber—as well as provide information to assist optimized timing of pacing pulses delivered during CRT. In a related form of this embodiment, a pressure sensor may be deployed in fluid communication with a RV chamber. As is known, direct measurement of developing pressure as well as derivatives and integrals thereof correlate to the hemodynamic status of the venous system of a patient. For example, at the moment that a maximum first derivative (commonly known as $dP/dt_{max}$) corresponds to the opening of the pulmonary arterial valve and thus provides an estimated pulmonary arterial diastolic (ePAD) pressure.

In addition to or in lieu of mechanical sensors such as accelerometers or pressure sensors, a metabolic sensor may be coupled to the reconfigurable multiple electrode medical electrical lead of the present invention. Such sensors may be coupled to distal or relatively proximal locations on the medical lead so that measurements may be made within the great vein or branches thereof, the region near the coronary sinus os, the right atrium (RA) and/or the superior vena cava (SVC) and the like. In one embodiment a metabolic sensor sensitive to oxygen or surrogates thereof (e.g., lactate, hydrogen peroxide, and the like) provides information regarding the relative degree of oxygen perfusion to the myocardium, venous blood oxygenation and the like.

As with any of the sensors described herein discrete measurements may be stored and/or averaged over time to obtain trend information and minimum, maximum values and the like. When compared or temporally mapped to an internally-sensed electrogram (EGM) or measurements of intrathoracic impedance, additional insight into the patient's condition is readily available. For example, an acute cardiac ischemic event occurring in a portion of the LV may be detected by an oxygen sensor disposed in the great vein while the plurality of electrodes disposed in or about the LV provide signals indicative of those portions of the LV representing electrically non-responsive myocardium. Other of the electrodes in communication with the LV can be enlisted to provide pacing and/or sensing capability. In the event that the electrically non-responsive myocardium permanently ceases conducting depolarization and repolarization wavefronts (i.e., becomes an Ml) then the enlisted electrodes may be employed chronically without requiring clinical or surgical intervention. However, in the event that the myocardium fully regains electrical function, a prior or more common electrode or array of electrodes may be used to pace and sense LV activity. Also, in the event that the myocardium regains a portion of its prior electrical function one or more of the plurality of electrodes may be iteratively tested so that a new, optimized therapy delivery regime is constructed for the present condition of the LV.

As is well known, if an output signal from an accelerometer is mathematically integrated the velocity of the adjacent cardiac tissue is measured and displacement signals are available by performing a double mathematical integration of an acceleration signal. Comparing a prior and a recent displacement signal from an accelerometer disposed on the left lateral free wall (preferably disposed about the mid-basal portion of the LV), thereby providing an indirect measurement of LV volume (e.g., comparing systole and diastole volumes). As a result, the present invention provides structure and methods to detect curative effects of CRT and other therapies so that relatively complex (and costly in terms of energy usage) therapeutic regimes may be avoided when not necessary. If the displacement of the LV is reduced significantly, the detected depolarization patterns are relatively uniform, and the LV and RV are contracting in a synchronized manner, CRT delivery may cease with a mode-switch to a more physiologic single- or double-chamber pacing therapy (e.g., AAI, ADI, AAI/R, ADI/R, etc.) without detriment to the patient.

BRIEF DESCRIPTION OF THE DRAWINGS

FIG. 3A depicts an alternative, epicardial lead system coupled to a patient's heart.

FIG. 3B is a pair of schematic representations of discrete volumes of ventricular tissue with the upper representation depicting the relationship between location of coronary arteries and the discrete volumes and the lower representation illustrating a 17-segment model for a left ventricle (along with a proposed naming convention for said segments).

FIG. 11 depicts a perspective view of proximal and distal end portions of a multiple electrode, fault tolerant medical electrical lead apparatus having a single lumen for receiving a pair of steerable guide wires that is constructed according to the present invention and may be used to practice the methods of the present invention.

FIG. 12A depicts a plan view of an alternate embodiment of a multiple electrode, fault tolerant medical electrical lead apparatus according to the present invention that may be used to practice the methods of the present invention, said lead having dual lumens for receiving individual distal end portions of the lead and wherein only said distal end portions each receive a steerable guidewire for accurate deployment of said distal end portions.

FIG. 12B is a perspective view of the distal portion of the lead depicted in FIG. 12A constructed according to the present invention and that may be utilized in conjunction with certain of the methods of the present invention.

FIG. 12C is an exploded view depicting another embodiment of a lead according to the present invention having a coaxial electrical conductor with a split transition (1:2) near a distal end thereof that also may be used to practice the methods of the present invention.

DETAILED DESCRIPTION OF THE INVENTION

Figure 1A:
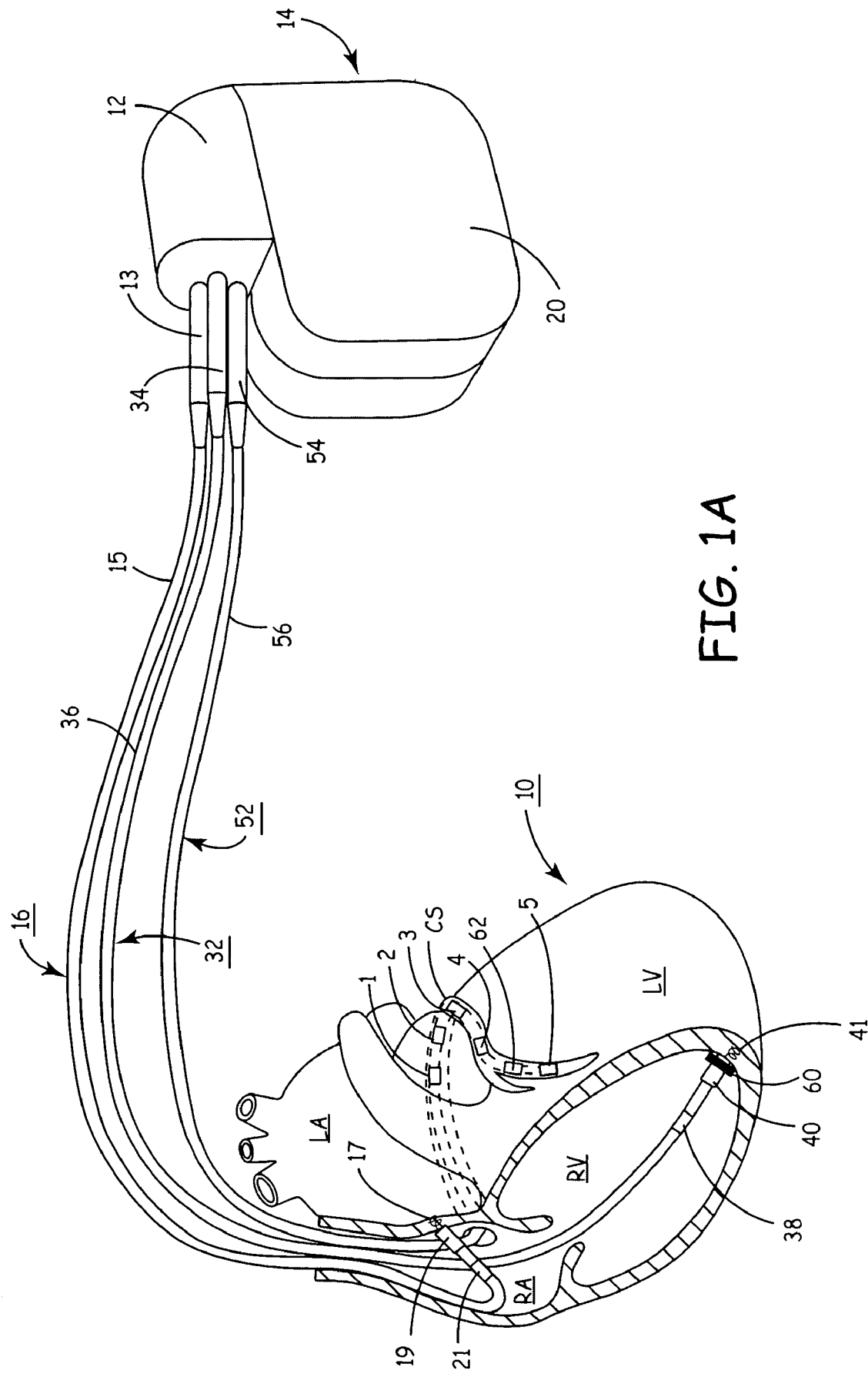
FIG. 1A depicts an exemplary implantable, multi-chamber cardiac pacemaker in which the present invention may be implemented.

The present invention provides a method and apparatus for assessing ventricular function on a chronic basis using a plurality of electrodes disposed in operative electrical communication proximate the LV. For certain methods according to the present invention at least one remote electrode disposed outside the LV is desirable (e.g., a canister-based, subcutaneous, pericardial, epicardial, coil type, RA, LA, or RV electrode, etc.). Optionally, at least one mechanical or metabolic sensor also operatively electrically couples to an implantable medical device (IMD) and provides cardiac performance information which can be used in conjunction with the multiple electrode lead system of the present invention.

The plurality of electrodes are spaced-apart so that a single electrode is disposed in electrical communication with a discrete volume of ventricular tissue. In one embodiment, the discrete volume of tissue is divided by planes as is known and used in the medical arts (e.g., apical, mid-basal, basal, anterior, lateral, and inferior or, until recently, posterior). Thus, according to the present invention, each electrode couples to appropriate sensing circuitry and essentially provides a localized electrogram (EGM) that, when compared to other EGMs, yields diagnostic information regarding cardiac function.

For example, by practicing the methods of the present invention an MI is readily detectable and, as a result, the operative electrodes delivering therapy to or near the region of the MI can be rerouted to deliver therapy elsewhere. In addition, the present invention provides a compact and convenient apparatus for performing a localized, study of dispersion of depolarization and repolarization wavefronts within cardiac tissue. The velocity and direction of such wavefronts provides valuable information regarding conduction status of the myocardium. Such information provides direct evidence of conduction anomalies (e.g., ectopic foci, reentry circuits, auxiliary passageways, etc.) without requiring visual, echocardiographic or tomographic inspection. That is, a clinician need not perform machine vision analysis (including electrophysiology study, echocardiographic examination, MRI or PET scans, fluoroscopy exposure or the like). Using such information a clinician can program electrode activation sequence(s) to counter conduction anomalies by tailoring therapy delivery based on the myocardial conduction status of a patient. On advantage of the conduction information is that it inherently incorporates current physiologic parameters reflecting overall autonomic tone of a patient regardless of possibly confounding factors (e.g., diet, exertion, cardiac and systemic drugs, and the like).

In addition, the reconfigurable, multiple electrode medical electrical lead operated according to certain aspects of the present invention provides fault tolerance (e.g., recording intrinsic and/or paced cardiac activity with electrode pairs not rendered ineffective by an MI) for sensing and/or therapy delivery. In multiple chamber embodiments, other electrode pairs may be used to complement the temporal cardiac information obtained with the multiple electrode of the present invention.

Moreover, in the event that one or more of the plurality of electrodes is rendered inoperable due to disengagement from adjacent myocardial tissue, electrical open or short circuit condition, of non-optimal disposition the electrode(s) and the like may be eliminated from a therapy delivery circuit. This aspect of the present invention offers a modicum of fault tolerance so that therapy delivery may continue unimpeded, possibly indefinitely. A clinician may reprogram the therapy delivery modality by interrogating the device or an automatic interrogation may occur pursuant to instructions stored in a computer readable medium.

Optionally, a mechanical or metabolic sensor may be operatively coupled to provide an additional complement of temporal information in sensing physiologic activity of a patient, monitoring a therapy delivery system, and optimizing therapy delivery. In one form of this embodiment, an accelerometer couples to a distal portion of a reconfigurable multiple electrode lead adapted for deployment within the great vein of the LV. The output signal from the accelerometer can be used to confirm one or more of the following: loss of capture (due to an MI or other cause) for a single pacing pulse or coupled pacing pulses (e.g., during extra-systolic stimulation therapy delivery), synchrony (or lack thereof) during delivery of a cardiac resynchronization therapy (CRT), presence of pulse-less electrical activity (also known as electro-mechanical dissociation), timing optimization for multi-site pacing therapy in a single chamber—as well as provide information to assist optimized timing of pacing pulses delivered during CRT. In a related form of this embodiment, a pressure sensor may be deployed into fluid communication with a RV chamber. As is known, direct measurement of developing pressure as well as derivatives and integrals thereof correlate to the hemodynamic status of the venous system of a patient. For example, at the moment that a maximum first derivative (commonly known as $dP/dt_{max}$) corresponds to the opening of the pulmonary arterial valve and thus provides an estimated (measurement of) pulmonary arterial pressure (ePAD).

In addition or in lieu of mechanical sensors such as accelerometers or pressure sensors, a metabolic sensor may be coupled to the reconfigurable multiple electrode medical electrical lead of the present invention. Such sensors may be coupled to distal or relatively proximal locations on the medical lead so that measurements may be made within the great vein or branches thereof, the region near the coronary sinus os, the right atrium (RA) and/or the superior vena cava (SVC) and the like. In one embodiment a metabolic sensor sensitive to oxygen or surrogates thereof (e.g., lactate, hydrogen peroxide, and the like) provides information regarding the relative degree of oxygen perfusion to the myocardium, venous blood oxygenation and the like.

As with any of the sensors described herein discrete measurements may be stored and/or averaged over time to obtain trend information and minimum, maximum values and the like. When compared or temporally mapped to an electrogram or measurements of intrathoracic impedance, additional insight into the patient's condition is readily available. For example, an acute cardiac ischemic event occurring in a portion of the LV may be detected by an oxygen sensor disposed in the great vein while the plurality of electrodes disposed in the LV provide signals indicative of those portions of the LV representing electrically non-responsive myocardium. Other of the electrodes in communication with the LV can be enlisted to provide pacing and/or sensing capability. In the event that the electrically non-responsive myocardium permanently ceases conducting depolarization and repolarization wavefronts (i.e., becomes an MI) then the enlisted electrodes may be employed chronically without requiring clinical or surgical intervention. However, in the event that the myocardium fully regains electrical function, a prior or more common electrode or array or electrodes may be used to pace and sense LV activity. Also, in the event that the myocardium regains a portion of its prior electrical function one or more of the plurality of electrodes may be iteratively tested so that a new, optimized therapy delivery regime is constructed for the present condition of the LV.

As is well known, if an output signal from an accelerometer is integrated the velocity of the adjacent cardiac tissue is measured, and if doubly integrated, displacement signal is available. Comparing a prior and a recent displacement signal from an accelerometer disposed on the left lateral free wall (preferably disposed about the mid-basal portion of the LV), thereby providing an indirect measurement of LV volume. As a result, the present invention provides structure and methods to detect curative effects of CRT and other therapies so that relatively complex (and costly in terms of energy usage) therapeutic regimes may be avoided when not necessary. If the displacement of the LV is reduced significantly, the detected depolarization patterns are relatively uniform, and the LV and RV are contracting in a synchronized manner, CRT delivery may cease with a mode-switch to a more physiologic, atrial-based, single- or double-chamber pacing therapy (e.g., AAI, ADI, AAI/R, ADI/R, etc.) without detriment to the patient.

The present invention provides for optimizing cardiac pacing intervals based on iterative measuring the response of various electrodes providing electrical stimulation to adjacent myocardium. The response may be detected with mechanical sensors (e.g., accelerometer coupled to a portion of LV free wall, pressure sensor for measuring pressure developed in the RV and/or great vein, etc.).

In some forms of the invention many different types of electrical stimulation therapy may be iteratively tested and compared to realize an optimum therapy delivery regime for a given patient. For example, uni- and bi-polar, mono- and bi-phasic pacing stimulation may be applied to each electrode coupled to the LV. In addition, substantially simultaneous pacing of a single chamber (e.g., LV) may be compared to a set of slightly time-delayed pacing of pairs or combinations of the electrodes (herein "cascade pacing") and, optionally based——at least in part—on the mechanical sensor output signals, an optimal multiple electrode pacing sequence implemented. As a reference for such iterative testing, the depolarization sequence of one or more intrinsically conducted cardiac cycles may be compared to the variously timed pacing cycles.

An additional advantage of monitoring intrinsic conduction at multiple sites is enhanced arrthymia detection; in particular, detection of potentially pathologic rhythms affecting or involving the LV. Such robust arrthymia detection is greatly enhanced by the ability to sense cardiac activity from a plurality of discrete electrodes. If spaced apart adequately so as not to be affected by local polarization currents typically following delivery of pacing energy, other electrodes can be used. Signals from such electrodes may carry a useful signal to noise ratio and thus do not need to be "blanked" thereby continuously sensing cardiac activity. For example, several electrodes of a decapolar (i.e., 10 unit) electrode set deployed into electrical communication with the LV can provide useful signals relating to cardiac activity if they are not used to deliver pacing therapy. Using such an electrode set for sensing-only activity relieves most of the typical energy management concerns for present day implantable medical devices. With respect to energy management during delivery of pacing therapy, the inventors believe that the present invention offers advantageous reduced pacing energy requirements (i.e., lower pacing thresholds) during pacing therapy delivery using more than about three discrete electrodes in a single chamber. This advantage applies in particular for multiple electrode LV pacing performed according to the present invention.

The present invention provides varied advances for an improved system for injecting electrical signals (e.g., direct current) and measuring resulting intrathoracic impedance values. Some clinically important physiologic parameters may be derived from discrete or mathematically derived impedance values for a patient, including minute ventilation (MV) and pulmonary fluid (or edema) status. In this context, in addition to the above-referenced related application, U.S. Pat. No. 5,876,353 to Riff et al., and U.S. Pat. Nos. 5,975,861 and 6,512,949 both to Combs et al. are all hereby incorporated by reference herein.

In one embodiment, the response to the different pacing (or impedance measuring) vectors is realized in a CRT delivery system that includes an implantable multi-chamber pulse generator and associated lead system wherein a LV coronary sinus lead or LV epicardial lead is provided with a sensor for detecting acceleration of the free wall, also referred to herein as "lateral wall," of the LV. In an alternative embodiment, a temporary, external pulse generator is coupled to temporary pacing leads including a reconfigurable, multiple electrode, LV temporary pacing lead equipped with an acceleration sensor (and/or a metabolic sensor).

The implantable or external system receives and processes the acceleration sensor signal to determine an index of cardiac activity based on LV [free wall] acceleration (LVA) during isovolumic contraction. Signal processing is performed to measure the acceleration signal and derive one or more signal parameters as indices of cardiac activity. In a preferred embodiment, the maximum amplitude of the first acceleration peak occurring during the isovolumic contraction phase is determined as the cardiac activity index. The cardiac activity index can be stored with other parametric or physiologic data for monitoring and/or diagnostic purposes.

During an automated, iterative testing routine, a cardiac therapy is optimized based on the LVA index of cardiac activity. In one embodiment, CRT is optimized by executing an iterative optimization method which includes the iterative inter-chamber optimization process described and depicted herein and optionally applying varying interventricular (i.e., ventricular-ventricular or "V-V") intervals and determining the peak LVA during isovolumic contraction. For example, the single, dual, or multiple electrode stimulation timing sequence for the LV (and, optionally, V-V interval) producing the greatest maximum amplitude of the first acceleration peak occurring during isovolumic contraction is selected for delivering CRT. This timing sequence (optionally including V-V interval timing) produces optimum interventricular synchrony and provides long-term, closed-loop CRT control. If the present invention is implemented to provide such optimum CRT control for heart failure patients, it is believed that the NYHA Class of such patients may improve over time (e.g., from NYHA Class IV to NYHA Class III or NYHA Class II). The present invention may enhance the ability to monitor and respond to the effects of so-called "reverse remodeling" wherein in response to chronic CRT: the shape of the heart, the size of the heart and/or the cardiac function for a patient in heart failure improves measurably over time.

The present invention is generally practiced with a plurality of electrodes deployed tranvenously so that at least one electrode electrically couples to a maximum number of discrete parts of a coordinate system of a cardiac chamber of interest. An existing cardiac coordinate system may be employed (describing cardiac features from a basal to apical perspective as well as an anterior to inferior—formerly posterior—perspective). However, according to the present invention any arbitrary coordinate system defining at least three discrete volumes of a chamber may be used. The inventors recommend use of the proposed standard for myocardial segmentation and nomenclature as published by Cerqueira et al. in an article published in the Jan. 29, 2000 edition of *Circulation* magazine and entitled, "Standardized Myocardial Segmentation and Nomenclature for Tomographic Imaging of the Heart" as approved by the American Heart Association Science Advisory and Coordinating Committee in September 2001. In brief, this proposed standard recommends using the long axis of the LV and selected planes oriented orthogonal to the LV long axis with three approximately equal segments dividing the LV long axis. The three segments are called the apical, mid-cavity and basal with each of the mid-cavity and the basal segments divided into six equal circumferential volumes of tissue (each encompassing 60 degrees of radius). The six segments are: anterior, anteroseptal, inferoseptal, inferior, inferolateral and anterolateral. Although, as recognized by those of skill in the art, "posterior" or "postero" may be used (in lieu of "inferior" or "infero"). Since the RV and LV taper as toward the tip of the apex, only four apical segments surround the apical volume; namely, the apical anterior, apical septal, apical inferior, and apical lateral The apical cap consists of only muscle (no cavity) and is referred to as simply the apex.

In particular, the proposed standard provides for the assignment of segments to specific coronary artery territories; for example, the left anterior descending (LAD), the right coronary artery (RCA) and the left circumflex coronary artery (LCX). The inventors find this proposed standard helpful inasmuch as the location of coronary veins corresponds relatively closely to the location of the cardiac arteries. According to the present invention, one or more medical electrical leads each having a plurality of reconfigurable, addressable pace/sense electrodes coupled thereto are deployed into a portion of a one or more of the coronary veins so that at least one electrode is electrically coupled to a discrete volume of LV myocardium. Recognizing wide variability in cardiac physiology among patients—by example and without limitation—portions of any of the following coronary vein vessels may be used in practicing the present invention: a great cardiac vein, a posterior (or, pursuant to the proposed standard, inferior) cardiac vein, a middle cardiac vein, a small cardiac vein, an anterior cardiac vein, an oblique coronary vein, a left marginal coronary vein, and a coronary sinus. To the extent that no coronary vein traverses a particularly useful volume or portion of myocardium—from a therapy delivery or cardiac activity-sensing perspective—an epicardial lead may be coupled to said volume or portion.

As indicated hereinabove, the present invention is directed toward providing a reconfigurable, fault tolerant, multiple electrode method and related therapy delivery apparatus for monitoring and enhancing cardiac activity, including optimization of diverse cardiac therapies. The present invention may be embodied in an implantable cardiac pacing system including a single chamber, dual chamber, or multichamber pacemaker and associated leads adapted to be disposed in the LV.

FIG. 1A depicts an exemplary implantable, multi-chamber cardiac pacemaker 14 in which the present invention may be implemented. The multi-chamber pacemaker 14 delivers pacing pulses to one or more heart chambers as needed to control the heart activation sequence. The pacemaker 14 is shown in communication with a patient's heart 10 by way of three leads 16,32,52. The heart 10 is shown in a partially cut-away view illustrating the upper heart chambers, the right atrium (RA) and left atrium (LA), and the lower heart chambers, the RV and LV, and the coronary sinus (CS) extending from the CS os in the RA laterally around the atria to form the great cardiac vein 48, with branches that form several cardiac veins.

The pacemaker 14, also referred to herein as the implantable pulse generator (IPG), is implanted subcutaneously in a patient's body between the skin and the ribs. Three transvenous endocardial leads 16,32,52 connect the IPG 14 with the RA, the RV and the LV, respectively. Each of the RA and RV lead 16,32 has at least one electrical conductor coupled to a pace/sense electrode. According to the present invention, a plurality of individually addressable pace/sense electrodes 1–5 are electrically coupled to LV lead 52 and perform a wide variety of functions as more fully described herein. The depicted pace/sense electrodes 1–5 are only exemplary, in that more or less that five such electrodes may be used according to the present invention depending on the desired function of the IPG 14. While the IPG 14 is used to describe and depict the present invention, the IPG 14 may include high voltage therapy delivery circuitry and electrodes when configured as an implantable cardioverter-defibrillator (ICD). The electrodes 1–5 may function as unipolar electrodes coupled to a remote indifferent can electrode 20. As is known in the art, delivery of pacing therapy to one of electrodes 1–5 can travel a current path to indifferent electrode 20 to close the pacing circuit. The indifferent electrode 20 may comprise the entire exterior surface of the IPG 14 or a portion of the outer surface of the housing 20 of the IPG 14. Of course, the pace/sense electrodes may The pace/sense electrodes 1–5 of the LV and the remote indifferent can electrode 20 can be selectively employed to provide a number of unipolar and bipolar pace/sense electrode combinations for pacing and sensing functions. In addition, one or more high voltage coil-type electrodes may be coupled to lead 52, The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21 provided for achieving RA pacing and sensing of RA electrogram (EGM) signals.

Bipolar, endocardial RV lead 32 is passed through the RA into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38 provided for RV pacing and sensing of RV EGM signals. RV lead 32 may optionally include a RV wall motion sensor 60. RV wall motion sensor 60 may be positioned into or proximate the RV apex for detecting motion or acceleration of the RV apical region. Implantation of an acceleration sensor in the RV is generally disclosed in the above-cited U.S. Pat. No. 5,693,075 issued to Plicchi, et al.

In this illustrated embodiment, a multiple-electrode endocardial LV CS lead 52 passes through the RA, through the CS os and further into a cardiac vein to thereby deploy each of the pace/sense electrodes 1–5 into electrical communication with a discrete volume of tissue of the LV chamber. The electrodes 1–5 can be used for LV pacing (alone or in conjunction other cardiac chambers), sensing of LV electrogram (EGM) signals, and/or monitoring intrathoracic impedance. The LV CS lead 52 is coupled at the proximal end connector 54 fitting into a bore of IPG connector block 12. A small diameter unipolar lead body 56 is selected in order to lodge the distal LV CS pace/sense electrode 5 deeply in a cardiac vein branching from the great cardiac vein 48 or other suitable location given the distribution of the other electrodes 1–4.

Figure 3C:
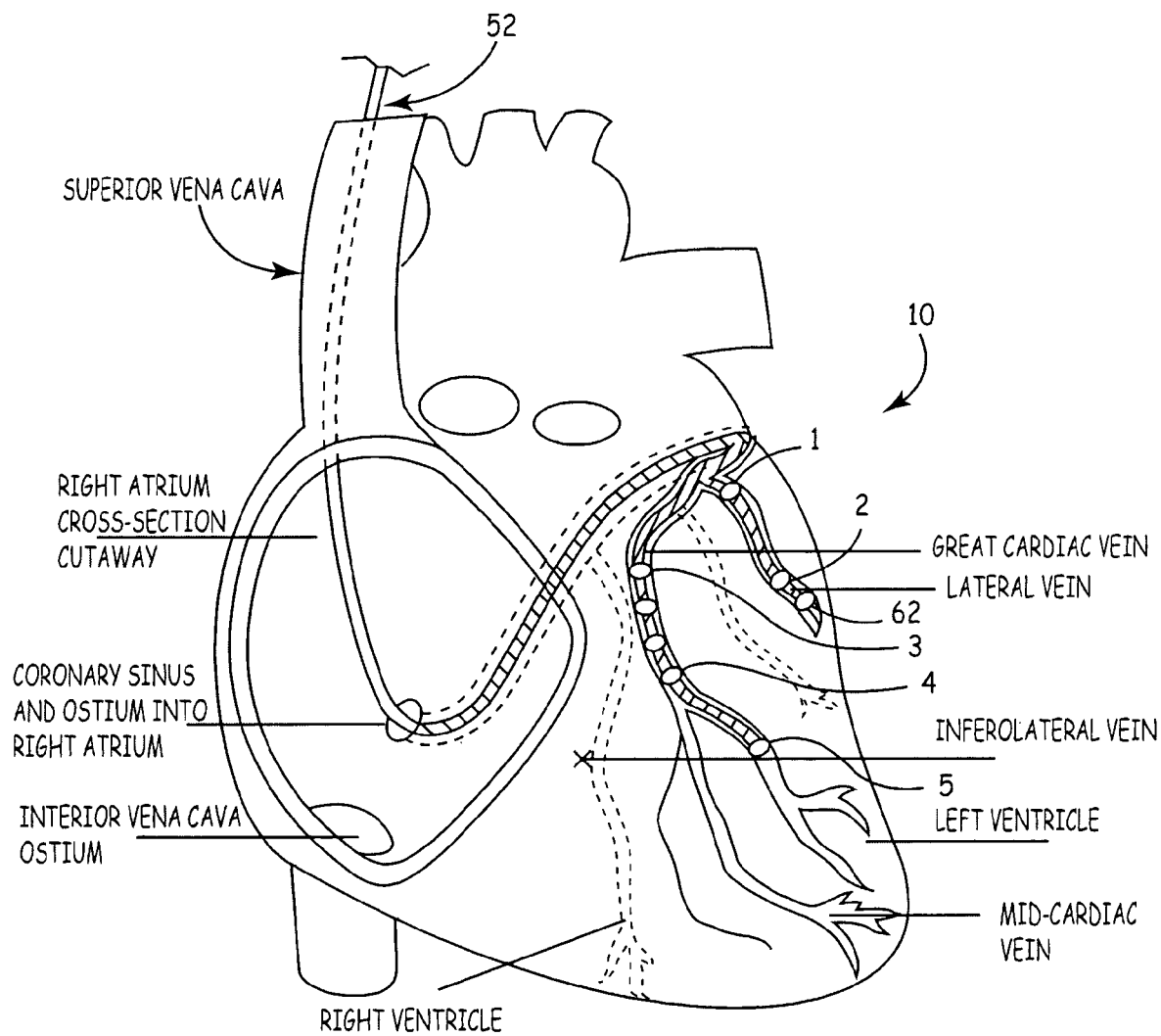
FIG. 3C is a schematic perspective view, with portions cut away, of a human heart 10 depicting the CS os of the RA and the great cardiac vein and branches therefrom (e.g., lateral vein, inferolateral vein(s), and mid-cardiac vein).

As depicted in FIG. 3C, any accessible portion of a cardiac vein (including the great cardiac vein) may receive one or more electrodes according to the present invention to provide electrical communication with as many discrete volumes of LV as reasonably possible. For example, the coronary sinus (CS), great cardiac vein, middle cardiac vein, the small cardiac vein and braches thereof may be used to provide the most complete electrical coverage of the LV. Of course, for some discrete volumes of LV myocardium one or more electrodes may be electrically coupled to the LV via a location in the RV (e.g., to reach the basal anteroseptal, the basal inferoseptal, the mid anteroseptal, the mid inferoseptal, or the apical septal locations). While in some of the illustrations up to about five discrete electrodes are depicted, the present invention should not be construed as so limited. In fact, according to the present invention on the order of seventeen discrete electrodes may each be deployed into electrical communication—each with a unique volume of LV myocardial tissue. However, the advantages of the present invention may be realized with as few as about three discrete electrodes, each electrode disposed in electrical communication with a one of a volume of basal tissue, a volume of mid tissue and a volume of apical tissue.

In accordance with the present invention, the coronary sinus lead 52 is provided with a sensor 62 capable of generating a signal proportional to the acceleration of the LV free wall. Sensor 62 is preferably embodied as a uniaxial, biaxial, or triaxial accelerometer contained in a capsule of a relatively small size and diameter such that it may be included in a coronary sinus lead without substantially increasing the lead diameter or impairing the ability to steer the lead to a LV pacing and sensing site. Radial acceleration may not be as valuable in assessing LV wall acceleration and optimizing pacing intervals as longitudinal acceleration, therefore, a uniaxial accelerometer may be adequate for these purposes. Sensor 62 may alternatively be provided as another type of sensor such as an optical, acoustical sensor or a sensor having piezoelectric, inductive, capacitive, resistive, or other elements which produce a variable signal proportional to LV acceleration or from which variations in LV acceleration can be derived. Sensor 62 is preferably located on CS lead 52 such that when CS lead 52 is positioned for LV pacing and sensing, sensor 62 is located approximately over the LV free wall at the mid-lateral to mid-basal segments. The depicted positions of the leads and electrodes shown in FIG. 1A in or about the right and left heart chambers are approximate and merely exemplary. For example, a LV acceleration sensor 62 may alternatively be located on CS lead 52 such that sensor 62 is positioned in the coronary sinus, in the great cardiac vein, or in any accessible inferior cardiac vein. Furthermore, it is recognized that alternative leads and pace/sense electrodes that are adapted for placement at pacing or sensing sites on or in or relative to the RA, LA, RV and LV may be used in conjunction with the present invention.

In a four chamber embodiment, LV CS lead 52 could bear a proximal LA CS pace/sense electrode positioned along the lead body to lie in the larger diameter coronary sinus adjacent the LA for use in pacing the LA and/or sensing LA EGM signals. In that case, the lead body 56 would encase an insulated lead conductor extending proximally from the more proximal LA CS pace/sense electrode(s) and terminating in a bipolar connector 54.

Figure 1B:
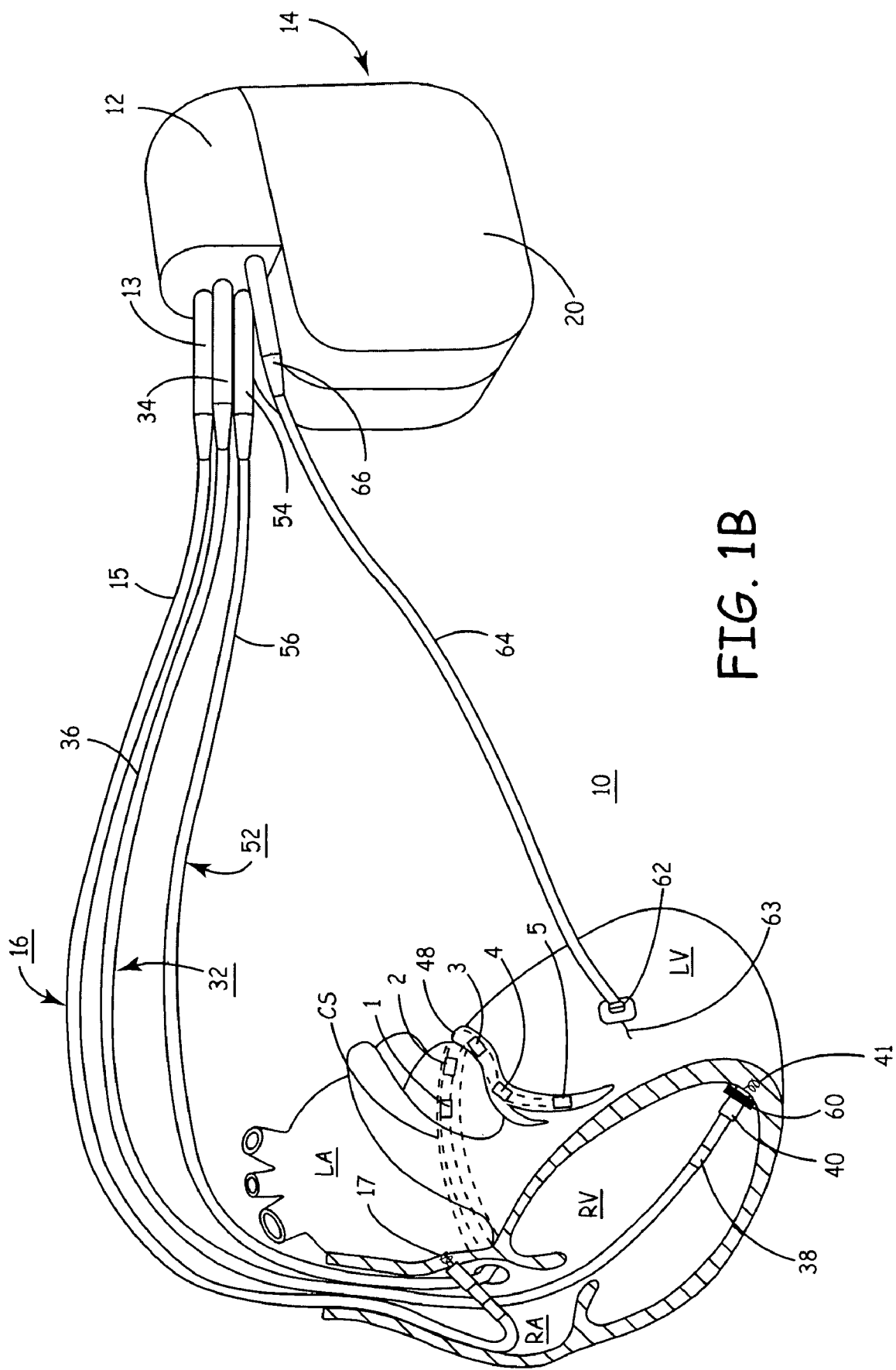
FIG. 1B depicts an exemplary implantable, multi-chamber cardiac pacemaker coupled to a patient's heart via transvenous endocardial leads and an additional LV epicardial lead equipped with acceleration sensor.

FIG. 1B depicts an exemplary implantable, multi-chamber cardiac pacemaker coupled to a patient's heart via transvenous endocardial leads and an additional LV epicardial lead equipped with acceleration sensor 62. Patients may already be implanted with a transvenous lead system that includes a coronary sinus lead 52 that is not equipped with an acceleration sensor. Such patients may benefit from the placement of an epicardial lead 64 equipped with an acceleration sensor 62 coupled to IPG 14 via a connector 66 so as to provide an LV acceleration signal for use in a closed-loop feedback system for providing resynchronization therapy at optimal pacing intervals.

Epicardial lead 64 is provided with a fixation member 63 which may serve additionally as a pacing and/or sensing electrode. In some cases, an epicardial lead may be preferred over a coronary sinus lead due to the difficulty in advancing a coronary sinus lead into a relatively small cardiac vein over the LV free wall. Placement of a coronary sinus lead can be a cumbersome task due to the tortuosity of the cardiac veins. Therefore, it may be desirable, at least in some patients, to provide an epicardial lead that can be positioned on the LV lateral wall for pacing, EGM sensing and acceleration monitoring, eliminating the need for a coronary sinus lead. Alternatively, it may be desirable to deploy a small diameter coronary sinus lead for LV pacing and EGM sensing with a separate LV epicardial lead positioned for sensing LV lateral wall acceleration.

The embodiment generally shown in FIG. 1B is particularly advantageous for use in selecting resynchronization therapy pacing sites. With epicardial lead 64 fixed at a desired location for assessing LV lateral wall acceleration, the effect of pacing at different locations in one or more heart chambers can be evaluated by deploying the transvenous (and/or epicardial) pacing leads 16 and 32 to different locations. In addition, during therapy optimization one or more of the multiple-electrodes coupled to CS lead 52 can be iteratively addressed for pacing therapy delivery or addressed in diverse combinations until an optimal response is identified based on analysis of the signal from LV acceleration sensor 62, other mechanical sensor (e.g., pressure transducer), and/or the LV EGM. In some embodiments, by providing acceleration sensor 62 on a separate, epicardial lead 64, the position of one or more of the pacing electrodes 1–5, provided on coronary sinus lead 52, may be adjusted independently of sensor 62. If the position of pacing electrodes 1–5 needs adjusting, acceleration sensor 62 may remain fixed at a desired measurement site on the LV lateral wall thereby allowing comparisons to be made between measurements repeated at the same location for different pacing intervals and/or pacing sites.

Figure 2:
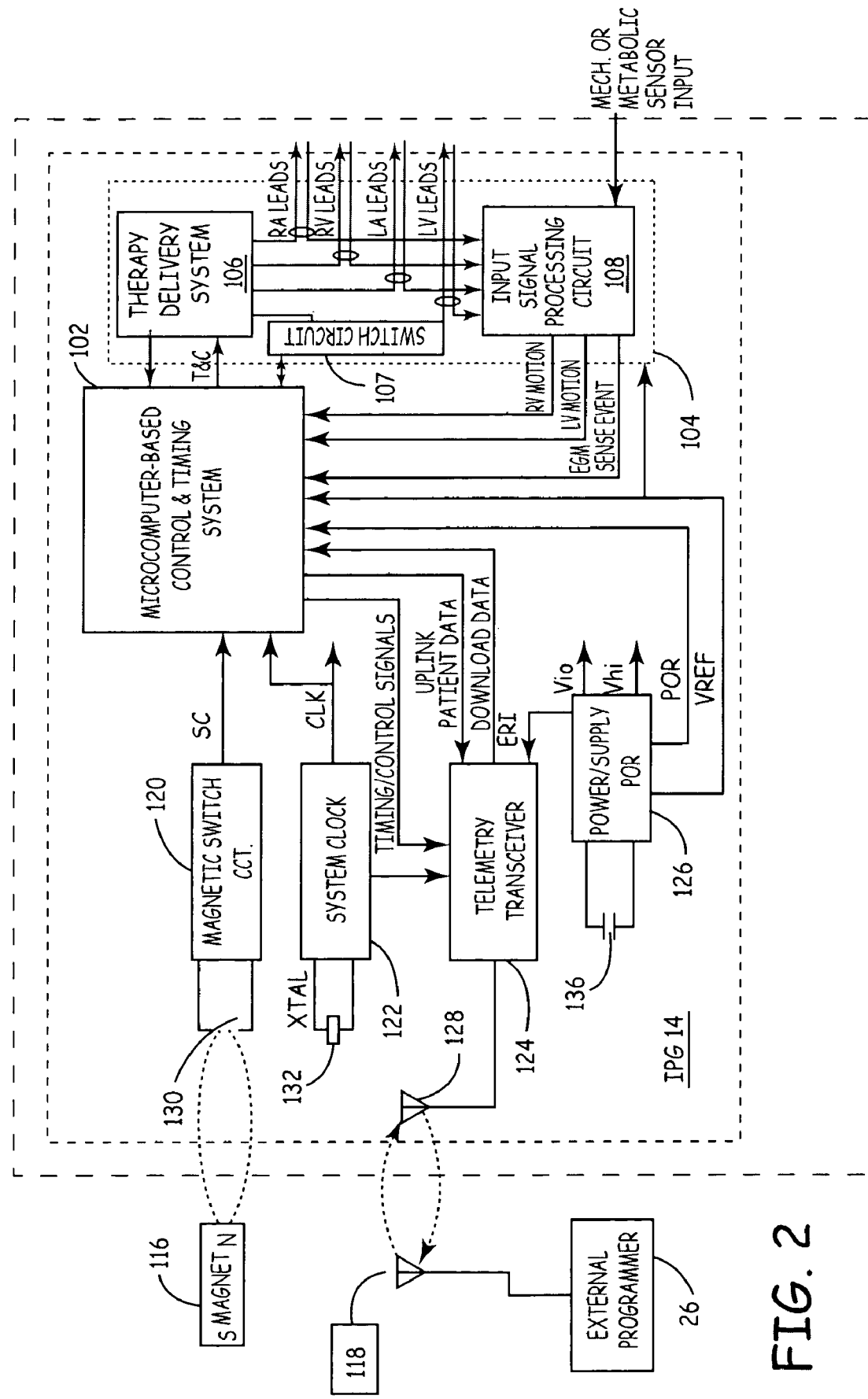
FIG. 2 is a schematic block diagram of an exemplary multi-chamber implantable pulse generator that provides delivery of a resynchronization therapy and is capable of processing LV acceleration signal input.

FIG. 2 is a schematic block diagram of an exemplary multi-chamber IPG 14, such as that shown in FIG. 1A or 1B, that provides delivery of a resynchronization therapy and is capable of processing LV acceleration signal input. The IPG 14 is preferably a microprocessor-based device. Accordingly, microprocessor-based control and timing system 102, which varies in sophistication and complexity depending upon the type and functional features incorporated therein, controls the functions of IPG 14 by executing firmware and programmed software algorithms stored in computer readable memory (e.g., associated RAM, DRAM, SRAM, ROM, EEPROM, etc.). Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IPG 14 can be accomplished with dedicated circuit hardware or state machine logic rather than a programmed microcomputer.

The IPG 14 includes interface circuitry 104 for receiving signals from sensors and pace/sense electrodes located at specific sites of the patient's heart chambers and delivering cardiac pacing to control the patient's heart rhythm and resynchronize heart chamber activation. The interface circuitry 104 therefore includes a therapy delivery system 106 intended for delivering cardiac pacing impulses under the control of control and timing system 102 to a electrodes of each deployed medical electrical lead. In the case of a reconfigurable, multiple electrode LV lead according to the present invention, a switching circuit 107 provides electrical communication between the therapy delivery system 108 and a one or more of the electrodes of the LV lead based on control signals from the control and timing system 102. The switching circuit 107 provides for simultaneous delivery of pacing stimulus to more than one electrode of the LV lead, timed (or "cascade") delivery of pacing stimulus, and variations thereof. In addition, when configured to deliver more than one pacing stimulus during a single cardiac cycle (e.g., so-called paired or coupled pacing), switching circuit 107 can provide the second (or coupled) pacing stimulus from the same (or a different) electrode that was used to provide a primary pacing stimulus. While not specifically depicted in FIG. 2, the present invention is intended to comprehend including more than one LV lead employed according to the methods of present invention. For example, an implantable epicardial LV lead having a plurality of electrodes coupled thereto can be used in lieu of or addition to an endocardial LV lead. According to one embodiment of the present invention, delivery of pacing pulses to a single chamber may be optimized before or after optimizing intra-chamber intervals.

Delivery of pacing pulses to two or more heart chambers is controlled in part by the selection of programmable pacing intervals, which can include atrial-atrial (A-A), atrial-ventricular (A-V), and ventricular-ventricular (V-V) intervals. In addition, according to the present invention an intra-chamber delay interval may be defined based upon sensed chamber activity and/or activity sensed by a mechanical sensor such as an accelerometer coupled to the heart. For example, when multiple, addressable electrodes are programmed to deliver a cascade of pacing stimulus to a single chamber (i.e., slight temporal delay between successive electrodes) an output signal from an accelerometer coupled to the heart can be used to optimize said intra-chamber delay interval. In lieu of or in addition to an accelerometer, a pressure sensor may be used to optimize intra-chamber delay intervals by maximizing (or minimizing) one or more pressure parameters.

Physiologic input signal processing circuit 108 receives cardiac electrogram (EGM) signals for determining a patient's heart rhythm. Physiologic input signal processing circuit 108 additionally receives signals from an LV mechanical sensor (e.g., wall acceleration sensor 62), and optionally an RV wall motion sensor 60, and processes these signals and provides signal data to control and timing system 102 for further signal analysis. For purposes of illustration of the possible uses of the invention, a set of lead connections are depicted for making electrical connections between the therapy delivery system 106 and the input signal processing circuit 108 and sets of pace/sense electrodes, acceleration sensors, and any other physiological, mechanical and/or metabolic sensors disposed in operative relation to the RA, LA, RV and LV.

Control and timing system 102 controls the delivery of bi-atrial, bi-ventricular, multi-chamber and/or multi-site cardiac pacing pulses (single, simultaneous, paired or coupled, etc.) at selected inter-chamber or intra-chamber intervals intended to improve heart chamber synchrony and cardiac sufficiency. The delivery of pacing pulses by IPG 14 may be provided according to programmable pacing intervals, such as programmable conduction delay window times as generally disclosed in U.S. Pat. No. 6,070,101 issued to Struble et al., incorporated herein by reference in its entirety, or programmable coupling intervals as generally disclosed in above-cited U.S. Pat. No. 6,473,645 issued to Levine. In addition, delivery of paired or coupled pacing (and related intervals and the like) are described in U.S. Pat. No. 5,213,098 issued to Bennett et al. and co-pending patent application Ser. No. 10/232,792, filed 28 Aug. 2002, the contents of each of which are hereby incorporated herein. Selection of the programmable pacing intervals can be based on an LV EGM or, optionally, using a determination of LV lateral wall acceleration derived from sensor 62 signals as will be described in greater detail below.

The therapy delivery system 106 can optionally be configured to include circuitry for delivering cardioversion/defibrillation therapy in addition to cardiac pacing pulses for controlling a patient's heart rhythm. Accordingly, leads in communication with the patient's heart may additionally include high-voltage cardioversion or defibrillation shock electrodes. In those embodiments of the present invention that include capability for measuring impedance, such high voltage leads may be used as part of an impedance injection circuit with respect to the canister of the IPG 14 or one or more of the electrodes deployed endocardially or epicardially according to the present invention. As is known in the art such defibrillation electrodes are typically coupled to high voltage circuitry including at least one capacitor for delivery of relatively low voltage cardioversion therapy and relatively high voltage defibrillation therapy.

A battery 136 provides a source of electrical energy to power components and circuitry of IPG 14 and provide electrical stimulation energy for delivering electrical impulses to the heart. The typical energy source is a high energy density, low voltage battery 136 coupled with a power supply/POR circuit 126 having power-on-reset (POR) capability. The power supply/POR circuit 126 provides one or more low voltage power (VIo), the POR signal, one or more reference voltage (VREF) sources, current sources, an elective replacement indicator (ERI) signal, and, in the case of a cardioversion/defibrillator capabilities, high voltage power (Vhi) to the therapy delivery system 106. Not all of the conventional interconnections of these voltages and signals are shown in FIG. 2.

Current electronic multi-chamber pacemaker circuitry typically employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The computer readable medium (e.g., RAM registers) included in microprocessor-based control and timing system 102 may be used for storing data compiled from sensed EGM signals, acceleration signals, pressure signals, and/or signals or parameters relating to device operating history or other sensed physiologic parameters for uplink telemetry transmission upon receipt of a retrieval or interrogation instruction via a downlink telemetry transmission. Criteria for triggering data storage can be programmed via downlinked instructions and parameter values. Physiologic data, including EGM and acceleration data, may be stored on a triggered or periodic basis or by detection logic within the physiologic input signal processing circuit 108. In some cases, the IPG 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IPG 14 to close switch 130 and prompt the control and timing system to deliver a therapy and/or store physiologic data. Event related data, e.g., the date and time and current pacing parameters, may be stored along with the stored physiologic data for uplink telemetry in a later interrogation session.

Uplink and downlink telemetry capabilities are provided to enable communication with either a remotely located external medical device or a more proximal medical device on or in the patient's body. Stored EGM, LV acceleration and/or pressure data as well as real-time generated physiologic data and non-physiologic data can be transmitted by uplink RF telemetry from the IPG 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemetering both analog and digital data between antenna 128 and an external device 26, also equipped with an antenna 118, may be accomplished using numerous types of telemetry systems known in the art for use in implantable devices.

The physiologic input signal processing circuit 108 includes at least one electrical signal amplifier circuit for amplifying, processing and in some cases detecting sense events from characteristics of the electrical sense signal or sensor output signal. The physiologic input signal processing circuit 108 may thus include a plurality of cardiac signal sense channels for sensing and processing cardiac signals from electrodes located in relation to a heart chamber and coupled to an operative sensing circuit. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of discrete events during a PQRST complex (esp. P-waves, R-waves and T-waves), respectively, and providing an atrial sense or ventricular sense event signal to the control and timing system 102. Timing and control system 102 responds in accordance with its particular operating system to deliver or modify a pacing therapy, if appropriate, or to accumulate data for uplink telemetry transmission in a variety of ways known in the art. Thus the need for pacing pulse delivery is determined based on EGM signal input according to the particular operating mode in effect. The intervals at which pacing pulses are delivered can be determined based on an assessment of the organization and velocity of sensed depolarization and repolarization wavefronts as well as LV wall acceleration data.

As such, input signal processing circuit 108 further includes signal processing circuitry for receiving, amplifying, filtering, averaging, digitizing or otherwise processing a mechanical LV signal (e.g., an LV wall acceleration sensor signal). If additional acceleration or other wall motion sensors are included in the associated lead system, for example a RV wall motion sensor, additional wall motion signal processing circuitry may be provided as needed. Acceleration signal processing circuitry is further provided for detection and/or determination of one or more acceleration signal characteristics such as maximum and minimum peak amplitudes, slopes, integrals, or other time or frequency domain signal characteristics that may be used as indices of acceleration (as well as velocity and displacement signals thereof. Acceleration data from an LV lateral wall acceleration sensor signal are made available to control and timing system 102 via LV MOTION signal line for use in algorithms performed for identifying pacing intervals producing optimal LV acceleration. If an RV wall motion sensor is present, an additional RV MOTION signal line provides RV wall motion signal data to control and timing system 102. In addition, other mechanical (or metabolic) sensor signals are available to control and timing system 102 via the "mech. sensor signal" line.

FIG. 3A depicts an alternative, epicardial lead system coupled to a patient's heart. Epicardial leads may be used in conjunction with either chronically implantable or temporary external pacing systems. In the embodiment shown, RV epicardial lead 80 is shown fixed via an active fixation electrode 82 near the apex of the RV such that the active fixation electrode 82 is positioned in contact with the RV epicardial tissue for pacing and sensing in the RV. RV epicardial lead 80 may optionally be equipped with an RV wall motion sensor 84 for detecting motion or acceleration of the RV apical region. LV epicardial lead 70 is shown fixed via a series of active fixation electrodes 6–9 in contact with portions of the LV such that each electrode (6–9) is positioned in contact with a discrete volume of LV epicardial tissue for pacing and sensing activity of the LV. As depicted, LV epicardial lead 70 is equipped with an optional acceleration sensor 74 coupled proximate electrode 6 for detecting acceleration of the LV free wall. While a single, multiple electrode epicardial lead is depicted more than one epicardial lead may be deployed according to the present invention. Epicardial lead systems may further include epicardial RA and/or LA leads. Various combinations of epicardial and transvenous endocardial leads are also possible for use with biventricular or multichamber cardiac stimulation systems.

In FIG. 3A, RV and LV epicardial leads 70 and 80 are shown coupled to an external, temporary cardiac pacing device 90. External pacing device 90 is a microprocessor controlled device including microprocessor 96 is implemented with associated RAM and ROM for storing and executing firmware and programmable software for controlling the delivery of pacing pulses to LV and RV pace/sense electrodes 6–9, 82, respectively. External device 90 receives signals from and delivers electrical pulses to LV and RV pace/sense electrodes 6–9, 82 via conductors included in LV epicardial lead body 76 and RV epicardial lead body 86. EGM signals, LV lateral wall acceleration signals, and optionally RV wall motion signals are received as input to input signal processing circuitry 94. Pacing impulses are delivered by output circuitry 92 as needed, based on sensed EGM signals, at intervals determined based on signals received from LV acceleration sensor 74 as will be described in greater detail below. It is recognized that an epicardial lead system such as that shown in FIG. 3 that includes an LV acceleration sensor and optionally an RV wall motion sensor may alternatively be used in conjunction with an implantable pacing system, such as the multi-chamber system described above and shown in FIGS. 1A and 2.

External device 90 of FIG. 3A and implantable device 14 of FIGS. 1A, 1B and 2 are shown to provide both sensing/monitoring and pacing delivery capabilities. Certain device features may be enabled or disabled as desired. For example, monitoring of LV lateral wall acceleration without delivery of a pacing therapy may be desired. Acceleration sensor signal data may therefore be received, processed and stored by an implantable or external device for later analysis and review by a clinician.

FIG. 3B is a pair of schematic representations of discrete volumes of ventricular tissue with the upper representation depicting the relationship between location of coronary arteries and the discrete volumes and the lower representation illustrating a 17-segment model for a left ventricle (along with a proposed naming convention for said segments). Since the coronary arteries closely correspond to the location of coronary veins, the inventors propose to following the naming convention and segmentation models in describing the present invention. For example, according to the present invention at least one electrode of a multiple-electrode medical lead should be disposed adjacent to as many of the segments (1–17 in FIG. 3B) as possible. Preferably, a minimum of at least three discrete electrodes are coupled to an apical-, mid- (or lateral) and a basal-segment. As previously noted, if one or more cardiac veins are not suitably close to a desired volume of LV tissue, a multiple electrode epicardial lead (such as lead 70 of FIG. 3A) may be used to obtain adequate electrical communication therewith.

FIG. 3C is a schematic perspective view, with portions cut away, of a human heart 10 depicting the CS os of the RA and the great cardiac vein and branches therefrom (e.g., lateral vein, inferolateral vein(s), and mid-cardiac vein). The depictions of FIG. 3B and FIG. 3C, illustrate how the cardiac veins can be used to place each of several electrodes (1–5) and an accelerometer (62) all coupled to a single lead 52 and in electrical communication with a discrete volume of LV tissue. As is known in the art, a medical electrical lead intended to couple to an interior portion of a cardiac vein (i.e., provide electrical communication between a pace/sense electrode and the vessel tissue) preferably operatively frictionally couples to the interior of the cardiac vessel. To that end, at least one part of the distal portion of each lead preferably includes some form of fixation apparatus. In one form of the invention, the apparatus comprises a curved, knuckle-like portion and in another an articulated arcuate member manually rotates into firm contact with the interior of a vessel.

A family of medical electrical leads designed for deployment through the CS is disclosed in U.S. Pat. No. 6,321,123 the contents of which are hereby incorporated by reference herein. The structures and methods disclosed in the '123 patent are particularly relevant to many forms of the apparatus of the present invention. Issued U.S. Pat. No. 6,567,704 also relates to medical electrical leads designed for deployment through the CS including provision for dispensing contrast media to enhance fluoroscopic viewing during deployment. The contents of the '704 patent are also hereby incorporated herein by reference. A published U.S. patent application to Dahl et al. entitled, "Bifurcated Lead System for a Cardiac Vein," (Pub. No. US 2002/0143380 A1) provides insight, structure and methods relating to the subject matter of the instant invention and is also hereby incorporated by reference herein. The above-identified three patent documents and the present patent application are all commonly owned by Medtronic, Inc. The multiple electrode reconfigurable medical leads usable with the present invention include so-called over-the-wire leads, side-wire leads (as described and depicted herein), as well as catheter delivered leads and combination over-the-wire and catheter delivery techniques.

Figure 4:
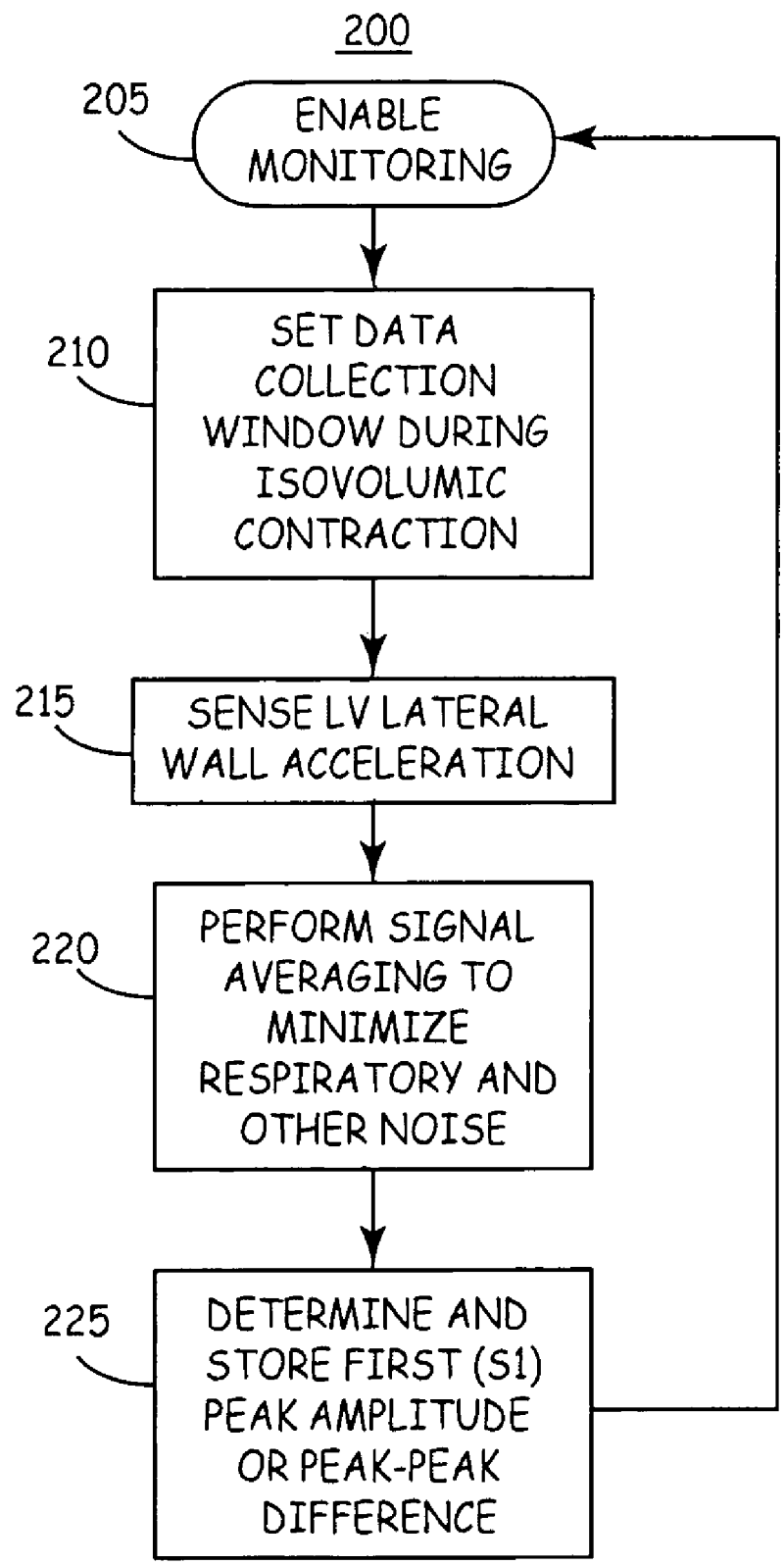
FIG. 4 is a flow chart providing an overview of a method for monitoring cardiac activity based on sensing LV lateral wall acceleration.

FIG. 4 is a flow chart providing an overview of a method for monitoring cardiac activity based on sensing LV lateral wall acceleration. Monitoring may be performed on an acute or chronic basis, using an implanted or external device in association with a LV lead equipped with an acceleration sensor as described above. Monitoring may be performed for diagnostic, prognostic, or therapy evaluation or optimization purposes. Therefore, monitoring may be performed post-operatively, during drug infusion, subsequent to a medical or device-delivered therapy, or on a chronic basis for ambulatory monitoring of patient status or therapy optimization and evaluation, Evaluation of LV activity is of interest for both diagnostic and therapeutic applications. Thus, it is recognized, that aspects of the present invention may be employed for cardiac monitoring purposes with or without optimization or evaluation of a therapy. As such, method 200 summarized in FIG. 4 may be implemented in an implantable or external device, such as the devices shown in FIGS. 1A, 1B, 3A, for monitoring LV activity by deriving and storing an index of cardiac activity based on an LV wall acceleration signal. The therapy delivery functions of such devices may be selectively disabled or, if enabled, the therapy optimization based on LV acceleration may be selectively enabled or disabled such that monitoring function only are enabled. Method 200 may alternatively be implemented in internal or external devices that do not include therapy delivery capabilities but, in association with an LV lead equipped with an acceleration sensor, are capable of processing and storing LV acceleration data.

Monitoring may be performed on a continuous, periodic or triggered basis. For example, LV function may be evaluated on a periodic basis such as hourly, daily, weekly, or otherwise. Additionally or alternatively, LV function may be evaluated on a triggered basis, which may be a manual or automatic trigger. Automatic triggers may be designed to occur upon the detection of predetermined conditions during which LV function evaluation is desired, such as a particular heart rate range, activity, or other conditions.

In one embodiment, LV acceleration is monitored continuously and storage of LV acceleration data is triggered upon the detection of predetermined data storage conditions, such as, but not limited to a base reading or material change in any of the following: a detected heart rate (HR), a level of activity, a measured impedance value, an MV signal, or a condition relating to LV acceleration. For example, LV acceleration may be sensed continuously, and, if an LV acceleration parameter crosses a threshold or satisfies other predetermined data storage criteria, LV acceleration parameter(s) are stored.

Manual triggers for LV acceleration sensing and/or data storage may be delivered by a clinician or by a patient, for example when the patient feels symptomatic. Methods for manually triggering the storage of physiological data in an implantable device are generally described in U.S. Pat. No. 5,987,352 issued to Klein, et al., hereby incorporated herein by reference in its entirety.

Method 200 begins at step 205 when monitoring is enabled according to a periodic, continuous or triggered mode of operation. At step 210, a data collection window is set. LV acceleration data is preferably collected during ventricular systole and most preferably during the isovolumic contraction phase. In one embodiment, the data collection window is a fixed time interval triggered by a sensed R-wave or an initial ventricular pacing pulse. The data collection window may begin immediately after, or following a predefined interval after, the sensed R-wave or ventricular pacing pulse and preferably extends through the isovolumic contraction phase, typically on the order of 30 to 180 ms in duration.

Figure 5:
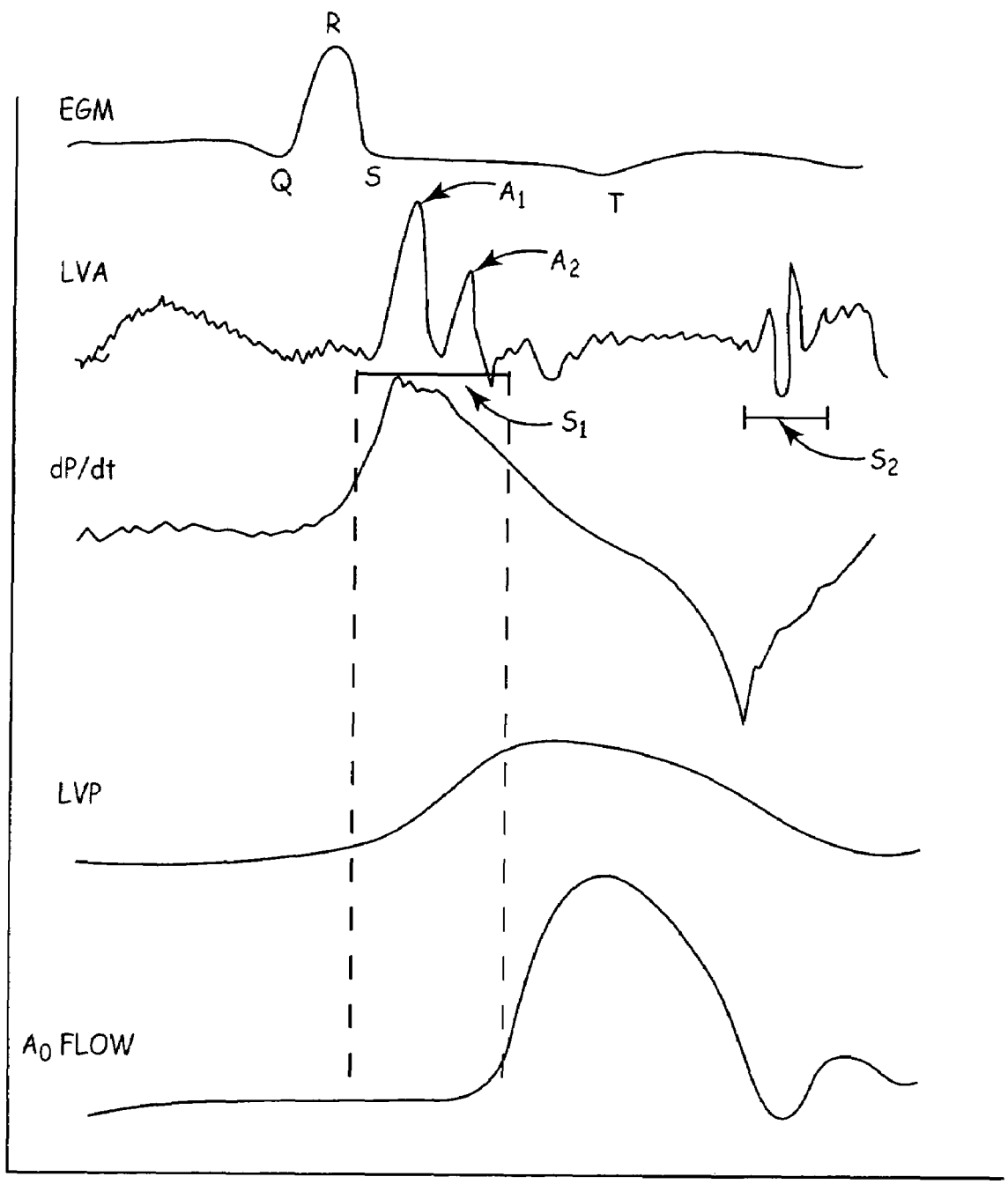
FIG. 5 is a plot of sample LV lateral wall acceleration data and simultaneous hemodynamic data acquired during one cardiac cycle.

FIG. 5 is a plot of sample LV lateral wall acceleration data and simultaneous hemodynamic data acquired during one cardiac cycle. The top trace represents a ventricular EGM signal showing a typical QRS complex of relatively large amplitude followed by a relatively smaller amplitude T-wave. The QRS complex marks the electrical activation of the myocardial tissue, causing depolarization and subsequent contraction of the myocardial fibers. The second trace represents the LV acceleration (LVA) signal obtained from an accelerometer placed to measure LV free wall acceleration. LVA is seen to reach a peak shortly after the QRS complex. The S1 phase indicated on the graph corresponds to the isovolumic contraction phase of ventricular systole and is associated with the first heart sound (S1) that occurs at the beginning of systole. LV free wall acceleration during this isovolumic phase, also referred to herein as "S1 phase", is not constant. In the example shown, LVA forms two peaks, $A_1$ and $A_2$, during the S1 phase. Varying conditions may result in one, two, three or possibly more LVA peaks during the isovolumic contraction phase. During isovolumic contraction, a large increase in LV pressure (LVP) is generated as shown on the fourth trace. LVP rises rapidly during the isovolumic phase as also shown by the third trace that is the first derivative of LVP (dP/dt). As LVP reaches a peak, the aortic valve opens, initiating the systolic ejection phase and an associated increase in aortic flow (Ao FLOW), shown on the bottom trace. After LVP falls, the aortic valve closes. During this phase, associated with the second heart sound, S2, the LVA signal exhibits one or more peaks that are typically lower in amplitude than the S1 peaks. In the preferred embodiment of the present invention, the LVA signal is acquired at least during at least a portion or all of the isovolumic, S1 phase.

Hence, in FIG. 4, method 200 senses the LV lateral wall acceleration signal at step 215 during the data collection window set at step 210 such that it extends approximately from the start to the end of the isovolumic contraction phase. Preferably the acceleration sensor is implanted in or proximate to the LV free wall as described above. More preferably, an LV acceleration signal is obtained from an accelerometer located on a coronary sinus lead or an epicardial lead positioned such that the accelerometer is situated over the mid-lateral, mid-basal or basal segment of the LV free wall. At step 215, the LV lateral wall acceleration signal is acquired over a number of cardiac cycles, preferably over at least one respiration cycle, such that signal averaging can be performed at step 220 to minimize respiration-related or other noise.

At step 225, the maximum amplitude or total excursion, referred to herein as the "peak-peak difference" of the first LVA peak occurring during the S1 phase is determined. This maximum amplitude or peak-peak difference is stored as a measure of cardiac activity. Additional information may be stored with the LVA data such as other sensed physiologic data and/or a time and date label and/or other parametric information. When method 200 is executed by an external system, LVA data may be displayed in real-time or stored and presented following a monitoring episode. When the method is executed by an implanted device, LVA data may be stored for later uplinking to an external device for display and review by a physician.

Figure 6:
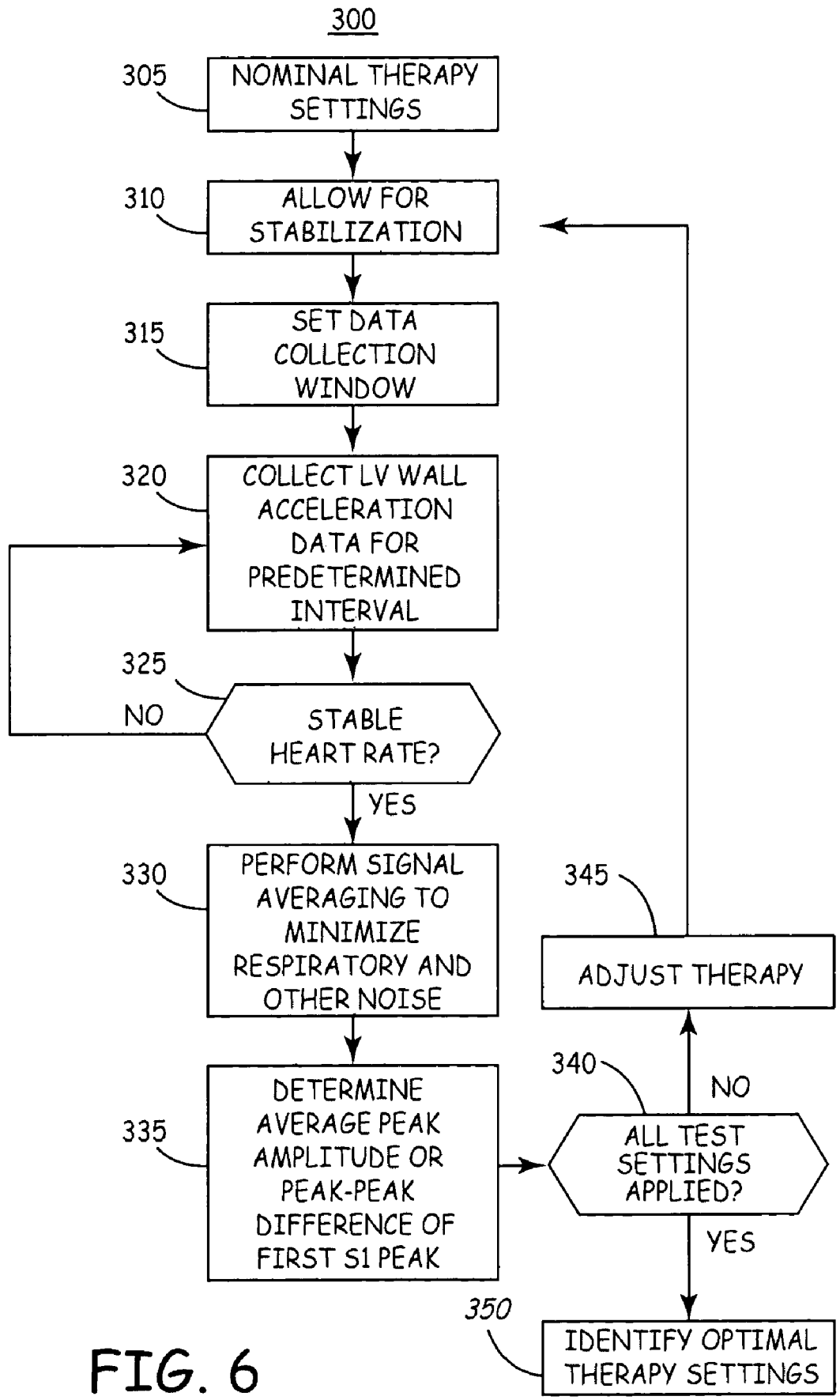
FIG. 6 is a flow chart summarizing steps included in a method for optimizing a therapy based on LV lateral wall acceleration.

As indicated previously, LV lateral wall acceleration may be monitored for therapy optimization purposes. FIG. 6 is a flow chart summarizing steps included in a method for optimizing a therapy based on LV lateral wall acceleration. Method 300 begins at step 305 wherein a therapy is delivered or administered at nominal settings or dosages. A therapy may be a cardiac pacing or resynchronization therapy or other cardiac rhythm management therapy, a therapy for treating myocardial ischemia, a medical therapy, or any other known therapy for improving cardiac activity, stroke volume, cardiac output (CO) and the like. As will be described, an iterative procedure may be performed for determining the optimal settings or dosages at which a therapy should be delivered for maximizing a desired cardiac performance criteria based, at least in part, on a measurement of LV free wall acceleration.

Depending on the type of therapy administered, an optional stabilization period may be provided at step 310 to allow the hemodynamic response to a change in therapy to stabilize prior to monitoring LVA. A stabilization period may range from several seconds, to minutes, hours or even days depending on the exemplary therapy being delivered. An exemplary therapy includes an extra-systolic stimulation (ESS) therapy also known as paired or coupled pacing and PESP therapy (as described in above-incorporated U.S. Pat. No. 5,213,098 to Bennett et al. and co-pending application Ser. No. 10/232,792). As is known, the effects of ESS therapy are manifest on at least an immediately subsequent cardiac cycle. Another therapy includes CRT requiring V-V optimization. With respect to CRT delivery with multiple site cascaded pacing stimulation, such a stabilization period should be set with consideration for the fact that an electrode disposed in a portion of the anterior cardiac vein will typically be delivered after other portions of the LV are stimulated. That is, the myocardium surrounding the anterior cardiac vein is known as a relatively "early" LV depolarization region and if stimulated prior to other LV regions may cause an adverse hemodynamic response. In such case, for example, to adjust the overall intrachamber depolarization of the LV the electrode(s) electrically coupled to anterior portions of the LV can be energized subsequent to other portions of the LV.

At step 315 a data collection window is set, preferably extending over the isovolumic contraction phase as described above. At step 320, the LVA signal is sampled during the data collection window for each cardiac cycle during a predetermined time interval or for a predetermined number of cardiac cycles. In an alternative embodiment, the LVA signal may be acquired continuously during the predetermined time interval or number of cardiac cycles and subsequently processed to separate components associated with the isovolumic contraction phase, and more particularly with the first acceleration peak during isovolumic contraction. The time interval or number of cardiac cycles preferably extends over at least one respiration cycle such that averaging of the LVA signal over a respiration cycle may be performed to eliminate variations in the LVA measurements due to respiration. In one embodiment, the start and stop of LVA data acquisition may be triggered by sensing a respiration cycle. Respiration may be detected based on impedance measurements or other methods known in the art.

At decision step 325, verification of a stable heart rate during the data acquisition interval is performed. Heart rate instability, such as the presence of ectopic heart beats, prior or acute MI, ischemia or other irregularities and the like, would produce anomalous LV data. As such, the heart rate preferably stays within a specified range. In one embodiment, heart rate stability may be verified by determining the average and standard deviation of the cardiac cycle length during the data acquisition period. The cardiac cycle length is determined as the interval between consecutive ventricular events including ventricular pacing pulses and any sensed R-waves. If the average cardiac cycle length or its standard deviation falls outside a predefined range, the data is considered unreliable. Data acquisition may be repeated by returning to step 315 until reliable data is collected for the current therapy settings.

At step 330, signal averaging is performed to minimize the effects of respiration-related or other noise. The signals acquired during each cardiac cycle over the data collection interval are averaged to obtain an overall average LVA signal. At step 335, one or more signal features are determined from the averaged LVA signal as an index of cardiac activity at the test therapy settings and stored in device memory with corresponding test setting information. As described above, the maximum amplitude or peak-peak difference of the first acceleration peak occurring during the isovolumic contraction phase (S1) is preferably determined at step 335.

If all therapy test settings have not yet been applied, as determined at decision step 340, the method 300 adjusts the therapy to the next test setting at step 345 and returns to optional step 310 and repeats steps 315 through 335 to determine the LVA index of cardiac activity for the new test setting. Once all test settings have been applied, the optimal setting is identified based on the stored LVA data at step 350. In one embodiment, the optimal setting corresponds to the maximum peak amplitude of the first LVA peak during isovolumic contraction.

Methods included in the present invention are particularly well-suited for optimizing the inter-ventricular (V-V) pacing interval during CRT. The inventors of the present invention has found that the amplitude of the first peak of the LVA signal during isovolumic contraction is dependent on the V-V interval during atrial-biventricular pacing and independent of the atrial-ventricular (A-V) interval.

Figure 7:
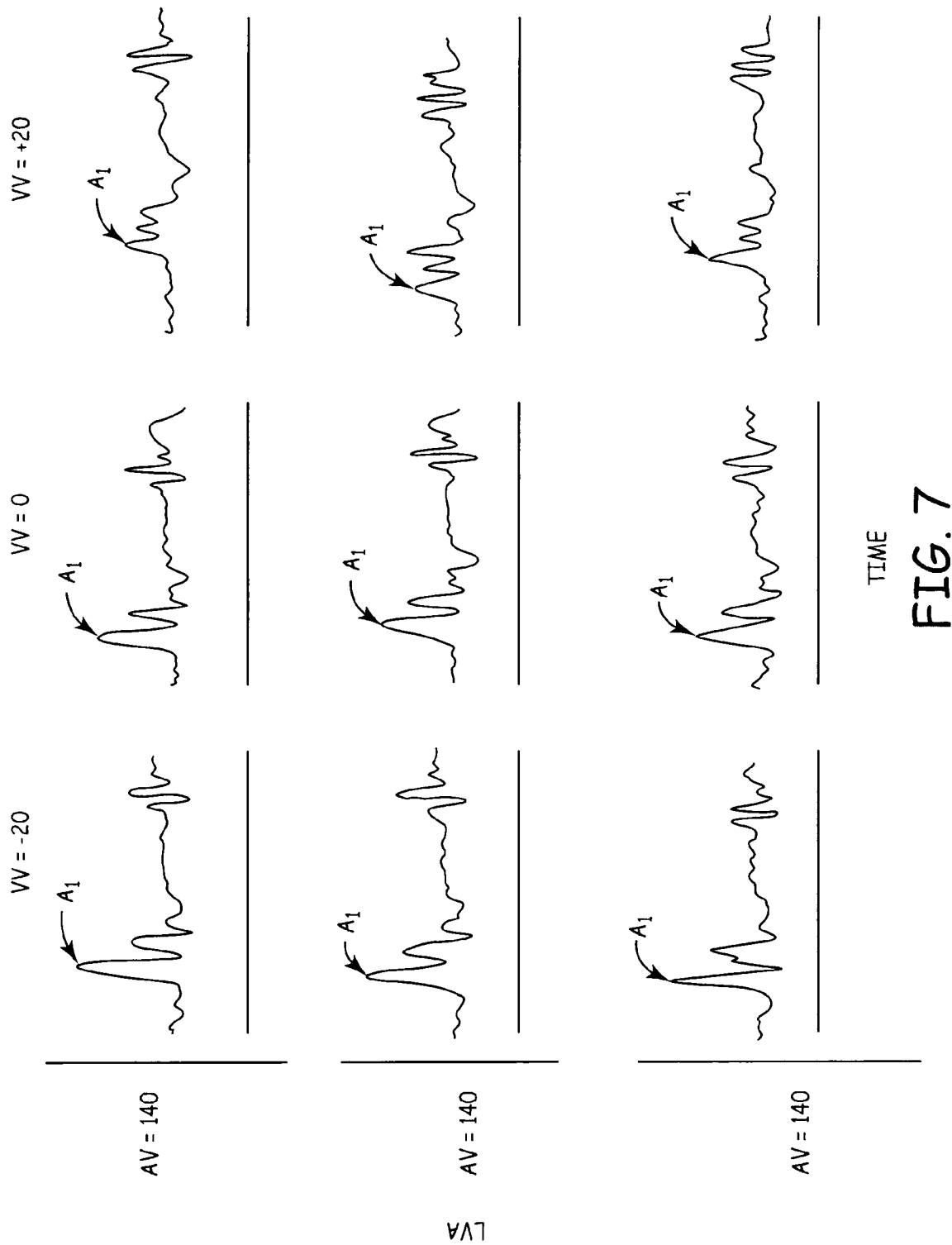
FIG. 7 is a set of graphs displaying the LV lateral wall acceleration signal acquired during atrial-biventricular pacing at varying A-V and V-V intervals.

FIG. 7 is a set of graphs displaying the LVA signal acquired during atrial-biventricular pacing at varying A-V and V-V intervals. Results from testing A-V intervals of 140, 170 and 200 ms are shown in the graphs moving from top to bottom with each column representing a fixed V-V interval. Results from testing V-V intervals of left-led pacing by 20 ms (−20 ms), simultaneous pacing of the left and RVs (0 ms), and right-led pacing by 20 ms (+20 ms) are shown in the graphs moving from left to right with each row representing a fixed A-V interval. The LVA signal is seen to vary in amplitude and morphology with varying V-V intervals (moving left to right). The LVA signal is seen to be unchanged with varying A-V intervals (moving from top to bottom). The maximum amplitude of the first LVA peak occurring during isovolumic contraction is indicated in each graph as $A_1$.

Figure 8:
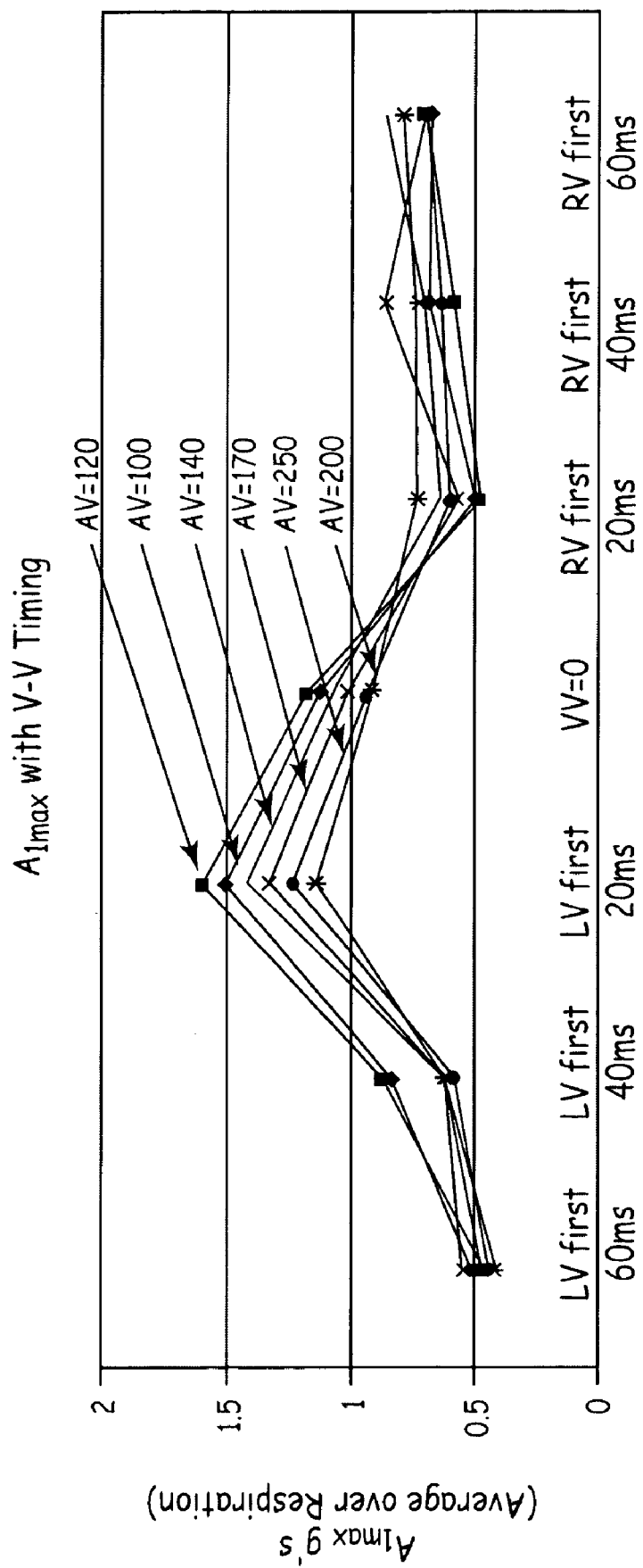
FIG. 8 is a plot of the maximum amplitude ($A_1$) determined from the LV acceleration signal during atrio-biventricular pacing at varying A-V and V-V intervals.

FIG. 8 is a plot of the maximum amplitude ($A_1$) determined from the LVA signal during atrio-biventricular pacing at varying A-V and V-V intervals. $A_1$ is plotted versus A-V interval for seven different V-V intervals (VVI). For a given V-V interval, the greatest magnitude for the $A_1$ amplitude remains the same for all the various A-V intervals. For a given A-V interval, $A_1$ amplitude is clearly dependent on the V-V interval and completely independent of A-V interval. Thus, the V-V interval during biventricular pacing can be optimized independently of the A-V interval based on the first LVA signal peak during isovolumic contraction. For the sample data set shown, a left-led V-V interval of 20 ms (−20 ms by convention) provides maximal LVA regardless of the A-V used to perform the iterative optimization testing.

It is recognized that other signal characteristic other than the maximum amplitude of the first peak may be correlated to LV activity and may be used for optimizing the V-V interval independent of the A-V interval during CRT or for optimizing other therapies. For example, a peak slope, an integral or other signal feature or fiducial point may be derived from the variable LVA signal during the isovolumic contraction phase and used as an index of cardiac activity for patient monitoring or therapy optimization procedures.

Figure 9:
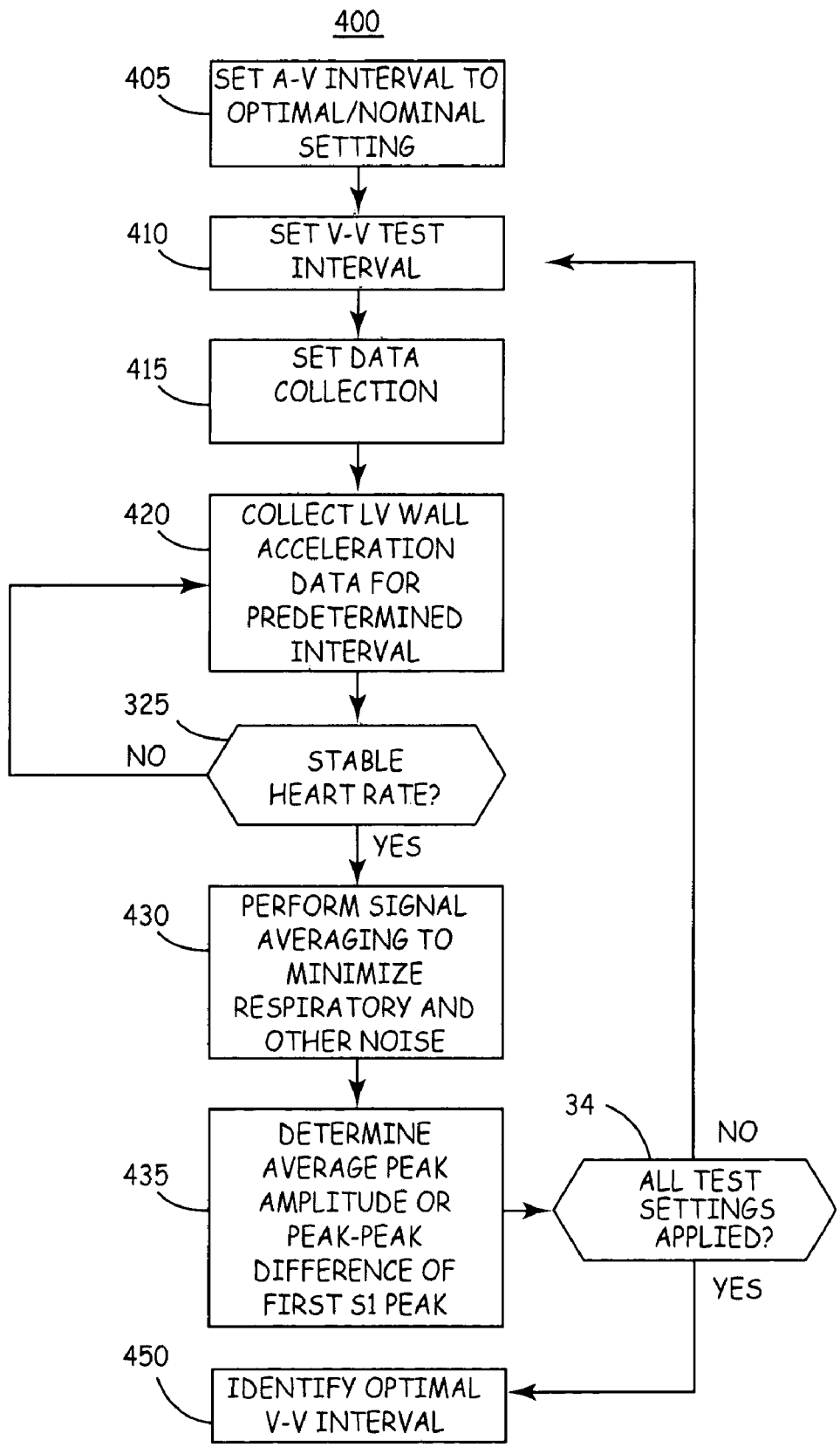
FIG. 9 is a flow chart summarizing steps included in a method for determining an optimal V-V interval based on LV acceleration.

FIG. 9 is a flow chart summarizing steps included in a method for determining an optimal V-V interval based on LV acceleration. At step 405, the A-V interval is programmed to a previously determined optimal or nominal setting. An A-V interval optimization procedure may be performed prior to optimizing the V-V interval to determine an optimal A-V interval setting. The A-V interval may be optimized based on methods known in the art. For example, an A-V interval may be selected as the shortest A-V interval that does not truncate ventricular filling based on echocardiographic evaluation. Alternatively, an optimal A-V interval may be selected based on RV apical motion as detected by an accelerometer placed at the RV apex. The A-V interval may alternatively be set to a nominal setting at step 405, and an A-V interval optimization method performed after optimizing the V-V interval.

At step 410, the V-V interval is set to a test interval. A range of test intervals are predefined and may be delivered in a random, generally increasing, or generally decreasing fashion. A range of test intervals may include intervals that result in the RV being paced prior to the LV and intervals that result in the LV being paced prior to the RV and simultaneous RV and LV pacing. In addition, two or more LV sense/pace electrodes may be simultaneously energized or they may be timed to send a temporally-offset cascade of pacing energy to the LV. A set of exemplary test intervals includes RV pacing 20 ms and 40 ms prior to LV pacing, simultaneous left and RV pacing (a V-V interval of 0 ms), and LV pacing 20 ms and 40 ms prior to the RV.

Method 400 proceeds to determine the optimal V-V interval in a manner similar to the iterative procedure for optimizing a therapy described above. A data collection window is set at step 415, and LVA data is collected for a predetermined time interval or number of cardiac cycles at step 420 during the data collection window applied to each cardiac cycle. After verifying a stable heart rate at step 425, signal averaging is performed at step 430 allowing an average peak amplitude or average peak-to-peak difference of the first acceleration peak ($A_1$) during the isovolumic contraction phase to be determined at step 435. $A_1$ is stored for the current test setting, and method 400 returns to step 410 to apply the next test setting until all test V-V intervals are applied as determined at decision step 440. The optimal V-V interval is identified at step 445 as the interval corresponding to the greatest $A_1$ amplitude.

When method 400 is executed by an external pacing system, LVA data is available for real-time display or stored and presented following an optimization procedure along with a recommended V-V interval. An attending clinician may program the V-V interval accordingly, or the external system may adjust the V-V interval to the optimal setting automatically. When method 400 for identifying an optimal V-V interval is executed by an implanted device, LVA data may be processed and stored for later uplinking to an external device for display and review by a physician. The implanted device can automatically adjust the V-V interval based on the identified optimal interval.

Figure 10:
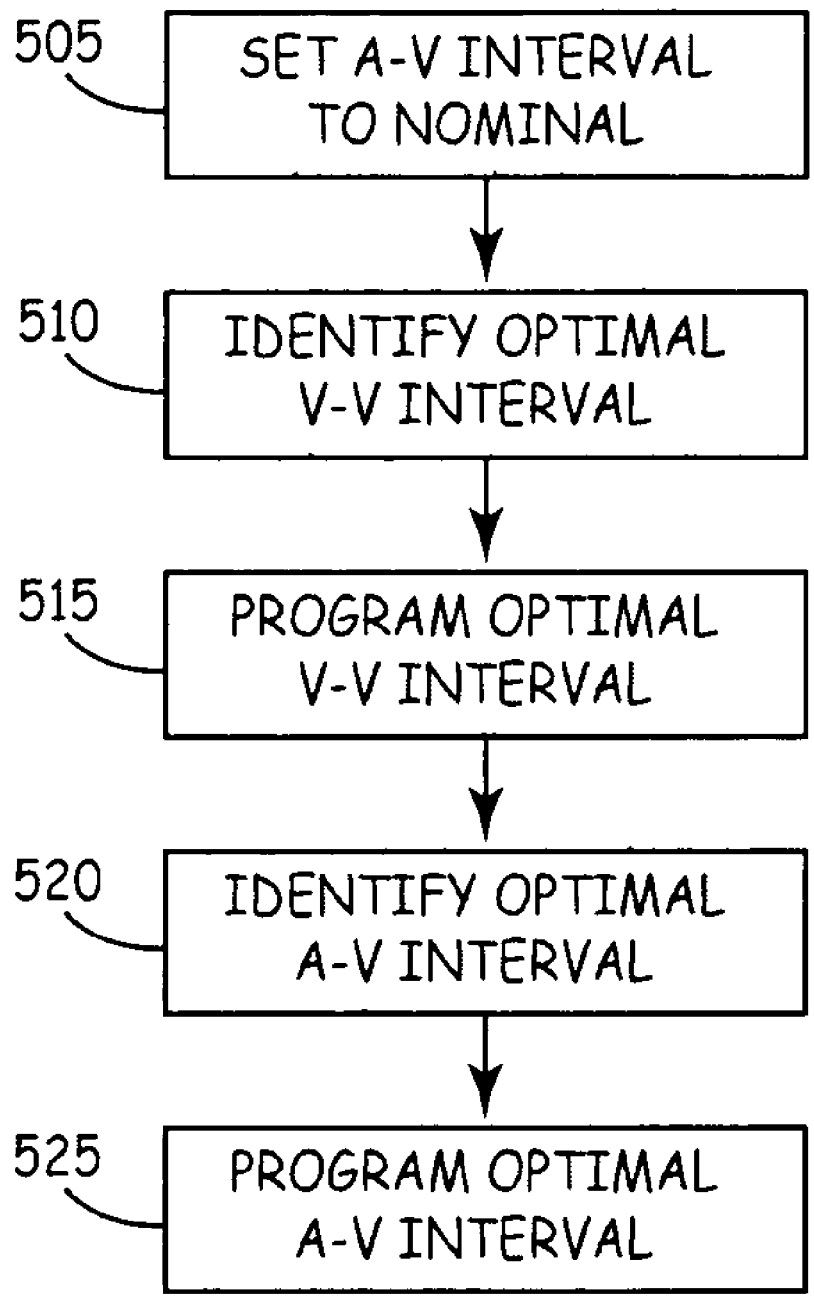
FIG. 10 provides an overview of a method for optimizing A-V and V-V intervals during CRT delivery.

FIG. 10 provides an overview of a method for optimizing A-V and V-V intervals during CRT. At step 505, an A-V interval is programmed to a nominal setting. At step 510, an optimal V-V interval is identified using method 400 of FIG. 9. At step 515, the V-V interval is automatically or manually programmed to the optimal setting. With the V-V interval maintained at the optimal setting, an A-V optimization procedure is performed at step 520. An optimal A-V interval is identified based on methods known in the art, as described previously. At step 525, the A-V interval is automatically or manually programmed to the optimal setting. Since the V-V interval can be optimized first, independently of the A-V interval according to methods included in the present invention, A-V and V-V interval optimization during multi-chamber cardiac pacing can be performed in a straight-forward, logical manner that is not limited or complicated by the effects that modulation of one parameter can have on the other.

While two (or more) leads may be used to deploy multiple electrodes into electrical communication with the LV, for a variety of reasons a single multiple electrode lead is desired. FIG. 11 depicts a perspective view of an exemplary multiple-electrode medical electrical lead 110 for use in conjunction with the present invention. The embodiment depicted in FIG. 11 has a single lumen portion 112 for receiving a pair of guidewires 114, 116, said single lumen portion 112 extending to a generally Y-shaped member 126 to help guide the wires 114, 116 into each distal end portion 118, 120 of the lead 110 where it divides into two parts. The end portions 118, 120 each have at least one electrode 122 disposed at or near the distal end of the end portions 118, 120. The guidewires 114, 116 provide for independent manipulation of the end portions 118, 120 as the lead 110 deploys into a cardiac vein of choice. That is, the guidewires 114, 116 are first deployed as desired and held in place as the lead 110 and the end portions 118, 120 slide along the wires 114, 116 to the selected location. The end portions 118, 120 each contain elongated electrical conductors (not depicted) coupled to each electrode 122. If the conductors 122 are configured to be independently addressable via the switching circuitry (107 depicted in FIG. 2) a single conductor provides electrical communication between each electrode 122 and the switching circuitry 107. Thus, the electrical conductors may comprise individually insulated wires (e.g., braided wire or the like). Each electrode 122 may be either independently addressable or, for some embodiments, may be coupled to a common current path extending to an IPG (not depicted). The embodiment depicted in FIG. 11 may be coupled to a connector module (not shown) of the IPG using one or more industry standard IS-1 connectors, depending if a uni-polar or true bi-polar arrangement is desired. For example, if two unipolar electrodes are to be activated by operative circuitry within the IPG, a single IS-1 connector may be used. On the other hand, if two bi-polar electrodes are to be operated a single IS-4 connector may be used (the IS-4 connector standard is presently being finalized) or two IS-1 connectors may be used. While not required, a means for enhancing the ability to push the lead 110 forward from just the proximal end can be added to the structure already described. One such means includes heat shrinkable tubing surrounding the elongated conductor(s) within the lead 110. One exemplary material for the enhancing the "pushability" of the lead 110 comprises ETFE.

FIG. 12A–12C depict another embodiment of a multiple electrode medical electrical lead 110 wherein a pair of side-mounted guide wires 114, 116 are used to deploy and position dual distal portions 118,120 of the lead 110 in two discrete braches of the cardiac veins. Coupled to an end portion of each of the distal portions 118, 120 is a tip electrode 122 having a hollow portion 124 for slideably receiving one of the guide wires 114, 116. Coupled to at least one distal portion 118, 120 (as depicted in 12A, distal portion 118) and in electrical communication via elongated conductors (not shown) with an IMD (not shown) is an accelerometer 62. Of course, other mechanical, biochemical and/or metabolic sensors may be employed in lieu of accelerometer 62. In one embodiment accelerometer 62 comprises a capacitive 6F capsule although a variety of other types of accelerometers and sensors may be used. At the junction of two distal portions 118, 120 an optional hollow portion of coiled conductor is 126' is configured to guide the wires 114, 116 into a respective one of the two proximal portions 118, 120 via a part of the body of the lead 110 with dual lumens 112 formed therein. The integral body portion of lead 110 proximal to the distal portions 118, 120 is preferably more resilient that the distal portions 118, 120 with a multi-conductor elongated coil disposed therethrough. To deploy the lead 110 depicted in FIGS. 12A–12C, the guidewires 114, 116 are each first positioned in a location within the cardiac veins and then the bi-lumen body advanced while the distal portions 118, 120 are maintained within the lumens 112. As the distal portions 118, 120 approach the desired location within the cardiac veins, the bi-lumen body may be optionally retracted so that the end portions 118, 120 are more readily manipulated to a final location. Once the final location is reached, the guidewires 114, 116 are fully retracted.

While not depicted in FIG. 11 or FIGS. 12A–12C, the lead 110 may be deployed at least partially using a delivery or guiding catheter.

Figure 13:
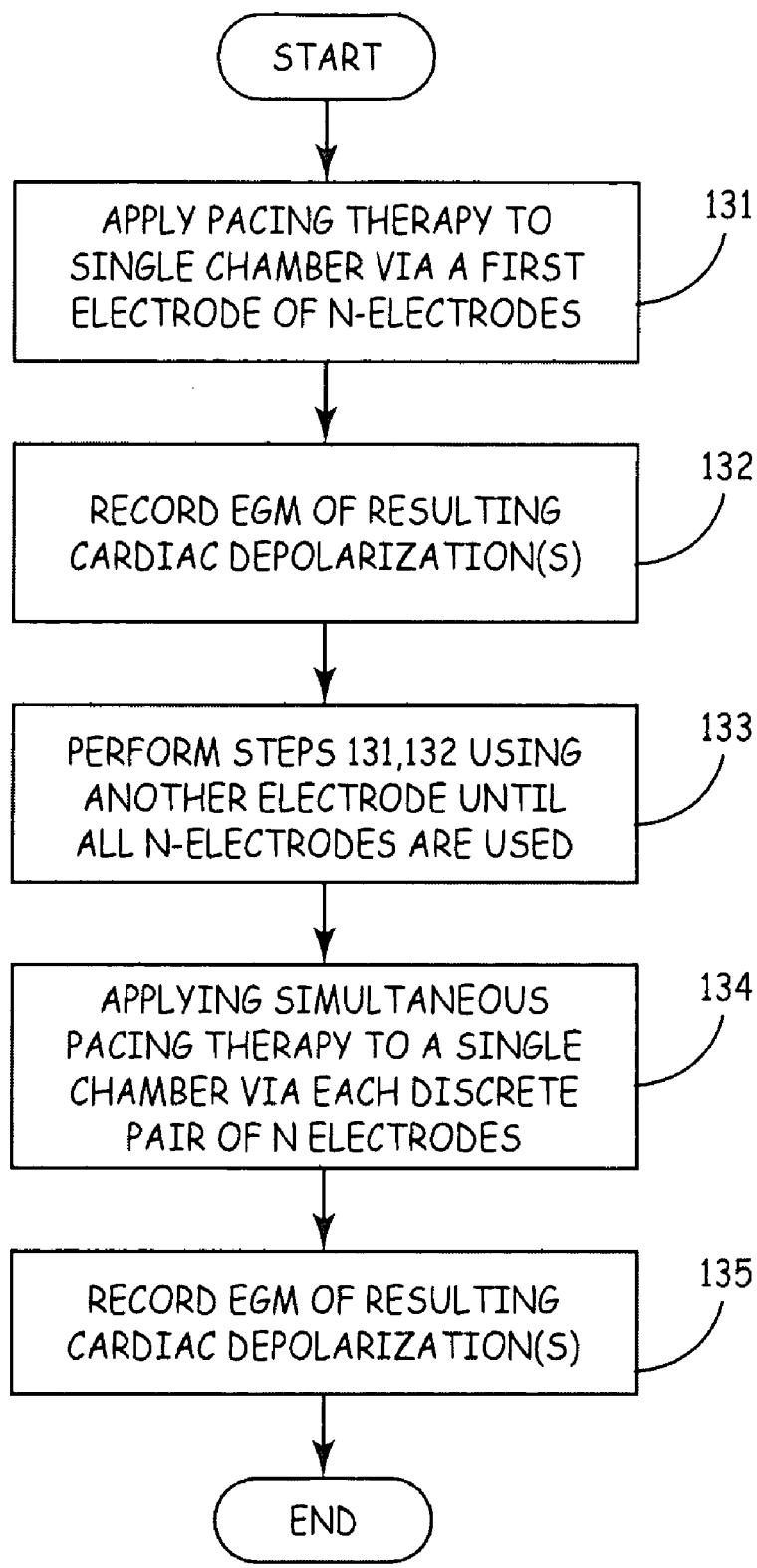
FIG. 13 is a flow chart depicting steps included in a method for applying therapy using a multiple electrode lead disposed in a single cardiac chamber wherein each lead may be used to delivery therapy, an EGM is recorded and then each discrete pair of electrodes are used to deliver therapy and another resultant EGM is recorded.

FIG. 13 is a flow chart depicting steps included in a method for applying therapy using a multiple electrode lead disposed in a single cardiac chamber and assessing EGM data to determine the optimal electrode to utilize for therapy delivery. At step 131 a pacing therapy is applied to a single chamber from a single electrode (of an n-electrode lead). At step 132 an EGM is recorded that captures the depolarization and repolarization activity of the single chamber. At step 133 the method returns to perform steps 131, 132 for each other of the n-electrodes with an EGM recorded for each electrode. At step 134 each pair of electrodes out of n-electrodes (n>1) are used to apply therapy to a single chamber and at step 135 the resulting EGM is recorded. The EGM waveforms may be digitized and compared and a preferred waveform topology identified as a relatively optimal example. Then, the electrode (or discrete pair of electrodes) that produced the relatively optimal EGM waveform is used to apply therapy.

Figure 14:
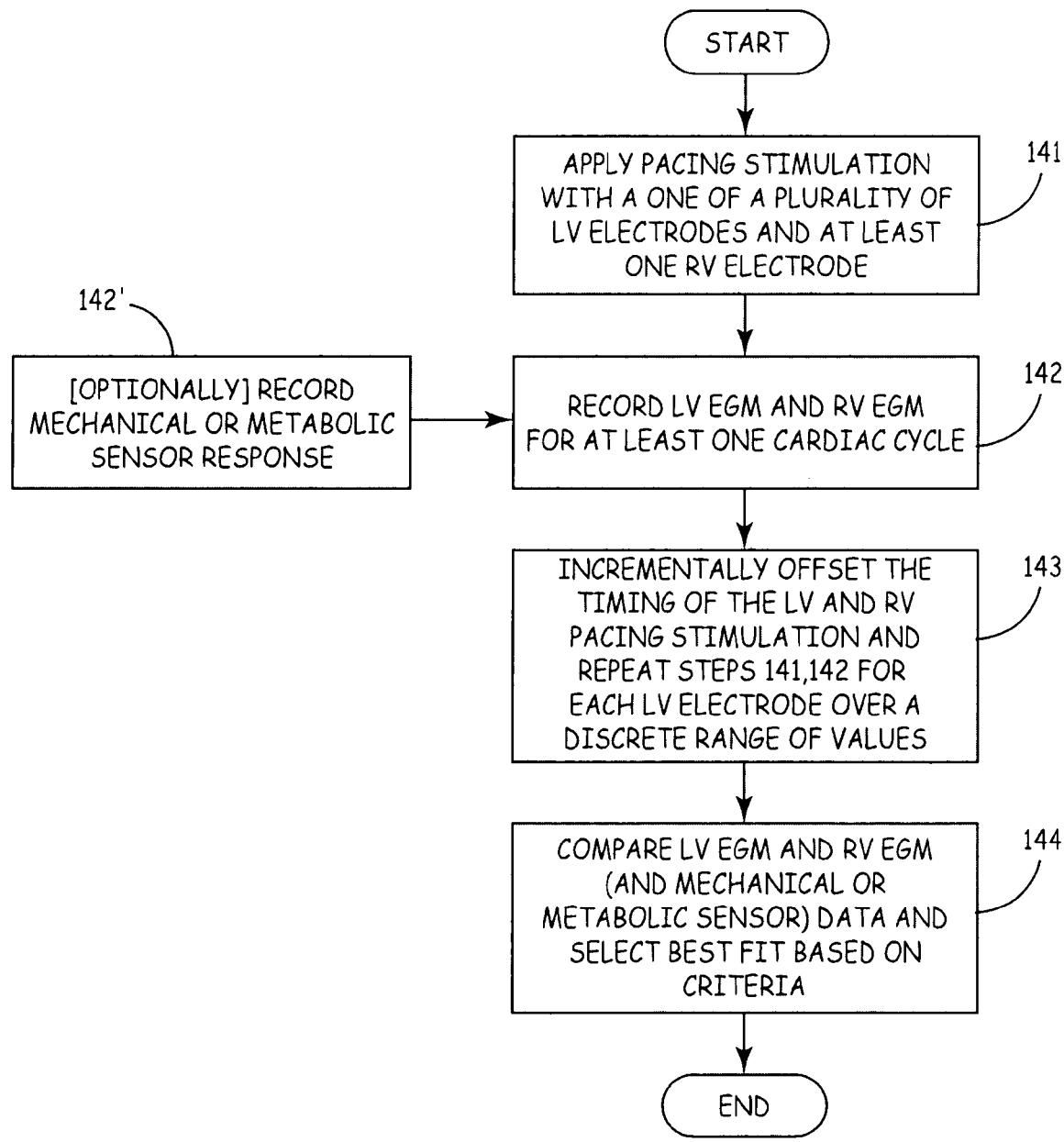
FIG. 14 is a flow chart depicting steps included in a method for determining if one or more electrodes are faulty and/or operatively coupled to a volume of myocardium by simultaneously sensing cardiac activity of a single cardiac chamber using a multiple electrode lead disposed in the chamber, recording an EGM for each electrode for at least one cardiac cycle, recording and/or comparing the EGMs to determine the status of the electrodes, and in addition determining the organization of depolarization and repolarization wavefronts in an attempt to identify a region of myocardium having one or more MI regions.

FIG. 14 is a flow chart depicting steps included in a method for optimizing a bi-ventricular cardiac pacing therapy such as CRT using various combinations of electrodes of a multiple electrode lead by applying therapy with a single LV electrode and a single RV electrode (step 141), recording a resultant EGM for at least one cardiac cycle (step 142), optionally recording a mechanical sensor response to said therapy (step 142'), incrementally offsetting the timing between the LV and RV electrode pacing stimulus delivery and repeating steps 141–142 (and optionally 142') over a discrete temporal range of values (step 143). Then the LV EGMs and RV EGMs are compared (including any mechanical or metabolic sensor data corresponding to the timing of the EGMs) to select the best fit of a discrete LV electrode and timing offset from an RV electrode to deliver CRT.

Figure 15:
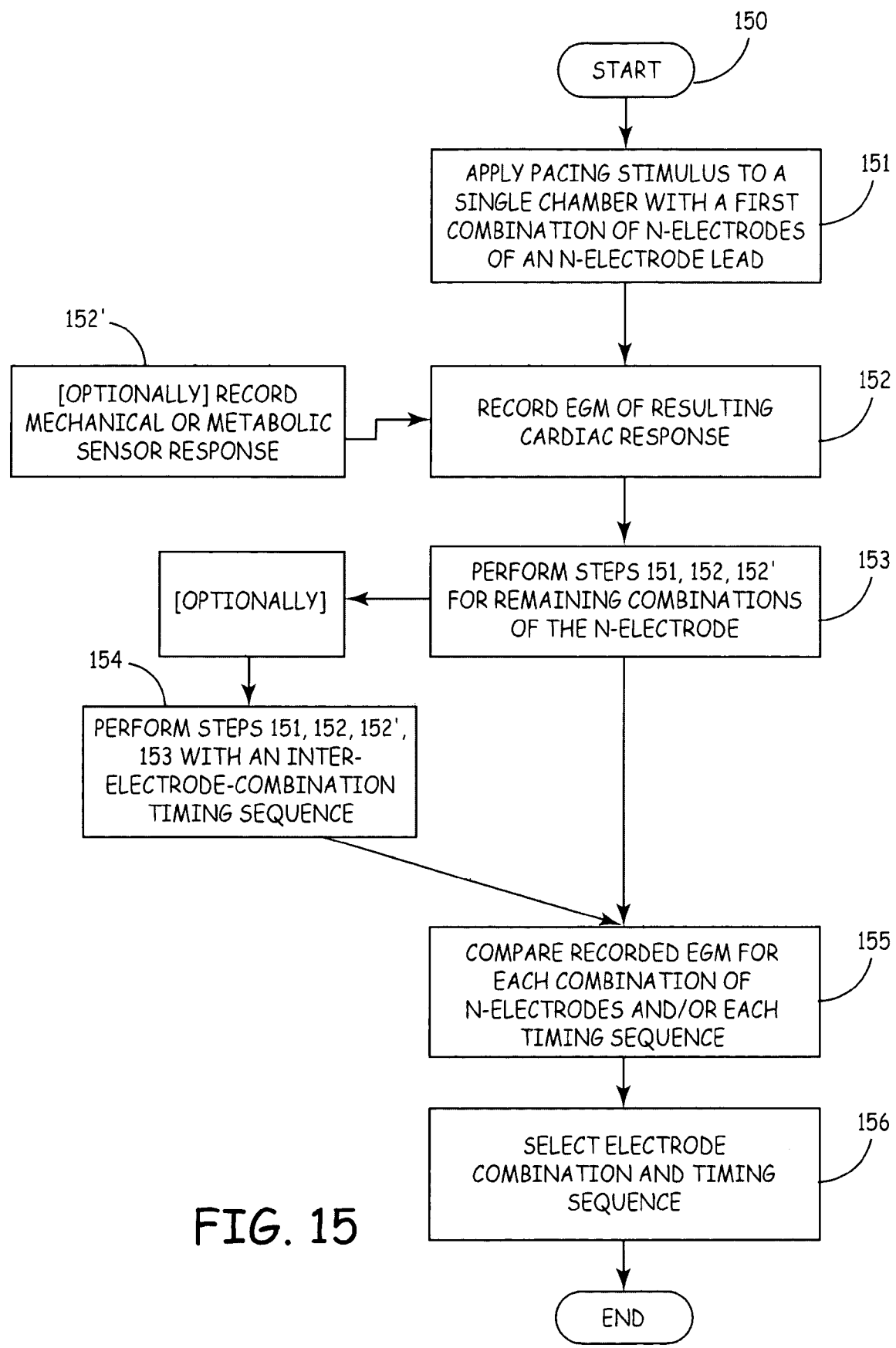
FIG. 15 is a flow chart depicting steps included in a method for optimizing a cardiac pacing therapy using various combinations of electrodes of a multiple electrode lead by applying therapy, recording a resultant EGM, optionally recording a mechanical sensor response to said therapy, optionally applying a cascaded pacing therapy having intra-chamber electrode delay intervals, comparing the resulting EGMs (with or without correlated sensor inputs) to identify a preferred temporal organization for chronically applying said therapy.

FIG. 15 is a flow chart depicting steps included in a method for optimizing a bi-ventricular cardiac pacing therapy such as a left-side-only ventricular pacing using various combinations of electrodes. A first combination of electrodes of an n-electrode multiple electrode lead are used to apply therapy (step 151). Then, the resultant EGM is recorded for at least one cardiac cycle (step 152), and optionally a mechanical and/or metabolic sensor response is also stored with the stored EGM (152'). At step 153 all the remaining combinations of the n-electrodes are used as steps 151 and 152 (and 152') are repeated. At step 154, an optional inter-electrode0combination timing sequence is used to perform steps 151–153. In either event, the recorded EGMs are compared for each combination of n-electrodes and, optionally, each timing sequence (from optional step 154). That is, at step 154, a so-called pacing cascade of pacing stimulus is applied to a single chamber using each combination of electrodes desired for testing. At step 156, an optimal single chamber electrode combination (and optionally, a cascade timing sequence for a given electrode combination) is selected to use when delivering a pacing therapy.

According to the present invention a method for determining if one or more electrodes are faulty and/or not operatively coupled to a volume of myocardium may be performed by sensing cardiac activity of a single cardiac chamber using a multiple electrode lead disposed in the chamber, recording an EGM from each electrode for at least one cardiac cycle, recording and/or comparing the EGMs to determine the status of the electrodes, and in addition, determining the organization of depolarization and repolarization wavefronts in an attempt to identify a volume of myocardium containing one or more MI regions. Such a method begins with each electrode of a multiple electrode lead operatively coupled to sensing circuitry. Then, an EGM is recorded (and stored for later retrieval) for each electrode during at least one cardiac cycle and the recorded amplitudes for each intrinsic or evoke response are compared. A baseline, or reference, condition or status is then used to determine if present EGM for a given electrode (or set of electrodes) has departed significantly, thus indicating a possible faulty electrode or disengagement of an electrode from an adjacent volume of myocardium.

Thus, a method and apparatus have been described for monitoring LV cardiac activity and optimizing a cardiac therapy based on LV lateral wall acceleration measured using a reconfigurable, multiple-electrode LV lead optionally equipped with an acceleration sensor and/or a metabolic sensor. The methods described herein may advantageously be applied in numerous cardiac monitoring or therapy modalities including chronic or acute applications associated with implantable or external devices.

As is known in the art, besides the transducers described hereinabove, other types of transducers may be used provided, in general, that such transducers are hermetically sealed, are fabricated (on least on the exterior surfaces) of substantially biocompatible materials and appropriately dimensioned for a given application. With respect to appropriate dimension, a transducer intended to transvenous deployment should be susceptible of catheter or over-the-wire delivery. Thus, the radial dimension should be on the order of less than about 11 French and preferably about less than eight French. Also, the transducer should be somewhat supple, and not too long, in the longitudinal dimension so that the transducer can safely navigate the venous system, pass through the coronary sinus and enter vessels branching from the coronary sinus (e.g., the great cardiac vein, inferior and anterior and other branches thereof and the like). These dimensions can be relaxed for a transducer intended for deployment though a portion of the chest (e.g., a thoracotomy) with an affixation mechanism adapted to mechanically couple adjacent the lateral wall. Two adjacent locations include the epicardium and the pericardium. The dimensions may be relaxed to a greater extent if the epicardial receives the transducer, and to a lesser extent, to a portion of the pericardium. As is well known, the pericardium is the membranous sac filled with serous fluid that encloses the heart and the roots of the aorta and other large blood vessels. One example of appropriate fixation apparatus for epicedial application is a helical tipped lead that is screwed into the surface of the epicardium. For pericardial fixation a sealing member (e.g., compressible gasket or opposing members on each side of the pericardial sac) may be used in addition to an active fixation member such as a helical tipped lead.

As is also known in the art related to sensors and transducers, accelerometers can be described as two transducers, a primary transducer (typically a single-degree-of-freedom vibrating mass which converts the acceleration into a displacement), and a secondary transducer that converts the displacement (of a seismic mass) into an electric signal. Most accelerometers use a piezoelectric element as a secondary transducer. Piezoelectric devices, when subjected to a strain, output a voltage proportional to the strain, although piezoelectric elements cannot provide a signal under static (e.g., constant acceleration) conditions. Important characteristics of accelerometers include range of acceleration, frequency response, transverse sensitivity (i.e. sensitivity to motion in the non-active direction), mounting errors, temperature and acoustic noise sensitivity, and mass.

One type of primary transducer, which describes the internal mechanism of the accelerometer, include spring-retained seismic mass. In most accelerometers, acceleration forces a damped seismic mass that is restrained by a spring, so that it moves relative to the casing along a single axis. The secondary transducer then responds to the displacement and/or force associated with the seismic mass. The displacement of the mass and the extension of the spring are proportional to the acceleration only when the oscillation is below the natural frequency. Another accelerometer type uses a double-cantilever beam as a primary transducer which can be modeled as a spring-mass-dashpot, only the seismic mass primary transducer will be discussed.

Types of secondary transducers, which describe how the electric signal is generated from mechanical displacement, include: piezoelectric, potentiometric, reluctive, servo, strain gauge, capacitive, vibrating element, etc. These are briefly described as an introduction for the uninitiated.

Piezoelectric transducers are often used in vibration-sensing accelerometers, and sometimes in shock-sensing devices. The piezoelectric crystals (e.g., often quartz or ceramic) produce an electric charge when a force is exerted by the seismic mass under some acceleration. The quartz plates (two or more) are preloaded so that a positive or negative change in the applied force on the crystals results in a change in the electric charge. Although the sensitivity of piezoelectric accelerometers is relatively low compared with other types of accelerometers, they have the highest range (up to 100,000 g's) and frequency response (over 20 kHz).

Potentiometric accelerometers utilize the displacement of the spring-mass system linked mechanically to a wiper arm, which moves along a potentiometer. The system can use gas, viscous, magnetic-fluid, or magnetic damping to minimize acoustic noise caused by contact resistance of the wiper arm. Potentiometric accelerometers typically have a frequency range from zero to 20–60 Hz, depending on the stiffness of the spring, and have a high-level output signal. They also have a lower frequency response than most other accelerometers, usually between 15–30 Hz.

Reluctive accelerometers use an inductance bridge, similar to that of a linear variable differential transducer to produce an output voltage proportional to the movement of the seismic mass. The displacement of the seismic mass in inductance-bridge accelerometers causes the inductances of two coils to vary in opposing directions. The coils act as two arms of an inductance bridge, with resistors as the other two arms. The AC output voltage of the bridge varies with applied acceleration. A demodulator can be used to convert the AC signal to DC. An oscillator can be used to generate the required AC current when a DC power supply is used, as long as the frequency of the AC signal is far greater than that of the frequency of the acceleration.

In servo accelerometers, acceleration causes a seismic mass "pendulum" to move. When motion is detected by a position-sensing device, a signal is produced that acts as the error signal in the closed-loop servo system. After the signal has been demodulated and amplified to remove the steady-state component, the signal is passed through a passive damping network and is applied to a torquing coil located at the axis of rotation of the mass. The torque developed by the torquing coil is proportional to the current applied, and counteracts the torque acting on the seismic mass due to the acceleration, preventing further motion of the mass. Therefore, the current through the torquing coil is proportional to acceleration. This device can also be used to measure angular acceleration as long as the seismic mass is balanced. Servo accelerometers provide high accuracy and a high-level output at a relatively high cost, and can be used for very low measuring ranges (well below 1 g).

Strain gauge accelerometers, often called "piezoresistive" accelerometers, use strain gauges acting as arms of a Wheatstone bridge to convert mechanical strain to a DC output voltage. The gauges are either mounted to the spring, or between the seismic mass and the stationary frame. The strain gauge windings contribute to the spring action and are stressed (i.e., two in tension, two in compression), and a DC output voltage is generated by the four arms of the bridge that is proportional to the applied acceleration.

These accelerometers can be made more sensitive with the use of semiconductor gauges and stiffer springs, yielding higher frequency response and output signal amplitude. Unlike other types of accelerometers, strain gauge accelerometers respond to steady-state accelerations.

In a capacitive accelerometer a change in acceleration causes a change in the space between the moving and fixed electrodes of a capacitive accelerometer. The moving electrode is typically a diaphragm-supported seismic mass or a flexure-supported, disk-shaped seismic mass. The element can act as the capacitor in the LC or RC portion of an oscillator circuit. The resulting output frequency is proportional to the applied acceleration.

In a vibrating element accelerometer, a very small displacement of the seismic mass varies the tension of a tungsten wire in a permanent magnetic field. A current through the wire in the presence of the magnetic field causes the wire to vibrate at its resonant frequency (like a guitar string). The circuitry then outputs a frequency modulation (deviation from a center frequency) that is proportional to the applied acceleration. Although the precision of such a device is high, it is quite sensitive to temperature variations and is relatively expensive.

The present invention may be embodied in discrete apparatus adapted to perform the physiologic monitoring and the therapy delivery methods hereof, the methods of fabrication for multiple-electrode leads, the methods of deployment and use, and as applicable, methods stored on a computer readable medium.

Thus, those of skill in the art will recognize that while the present invention has been described herein in the context of specific embodiments, it is recognized that numerous variations of these embodiments may be employed without departing from the scope of the present invention. The descriptions provided herein are thus intended to be exemplary, not limiting, with regard to the following claims.

The invention claimed is:

1. A multiple electrode, fault-tolerant medical electrical lead adapted for deployment into a portion of a coronary sinus, a great vein, or branches of the great vein, comprising:
   an elongated electrified biocompatible lead member;
   at least three spaced-apart electrodes coupled to a distal portion of the lead member and in electrical communication with a means for addressing each of said at least three spaced-apart electrodes; and
   a means for manually guiding said distal portion of the lead member into a portion of a coronary sinus, a great vein, or branches of the great vein so that each of said at least three spaced-apart electrodes are disposed in intimate electrical communication with a different discrete volume of cardiac tissue, wherein said distal portion comprises a bifurcated lead portion and wherein at least one of the at least three electrodes mechanically and electrically couples to the bifurcated lead portion; wherein at least one of the at least three electrodes comprise a tip electrode having a first axial bore formed through a portion of said tip electrode; and wherein the means for manually guiding said distal portion of the lead member comprises; a guide wire slidingly engaging said axial bore
   a second tip electrode having a second axial bore formed through a portion of said tip electrode; and wherein the means for manually guiding said distal portion of the lead member comprises a second guide wire slidingly engaging said second axial bore;
   a pair of guidewire lumens, each one of said pair of guidewire lumens formed in a lateral side portion of the bifurcated distal portion and wherein said first axial bore and said second axial bore are disposed spaced from an axial center of the first tip electrode and the second tip electrode, respectively, and generally in alignment with said pair of guidewire lumens; and
   a bi-lumen delivery catheter adapted to slidingly receive the bifurcated distal portion and wherein said first guidewire and said second guidewire are disposed outside said bi-lumen delivery catheter.

2. A medical lead according to claim 1, further comprising a resilient co-axial coil-type conductor disposed within a proximal portion of the medical lead, said co-axial coil-type conductor diverging into two independent coil-type conductors and wherein each of said two independent coil-type conductors are disposed in a separate one of the bifurcated portion of the medical lead.

3. A reconfigurable multiple electrode lead system, comprising:
   an elongated medical electrical lead and delivery system that delivers at least three individually addressable electrodes into more than one cardiac vein site along the epicardial surface of the ventricular wall, wherein each of said at least three individually addressable electrodes are configured to electrically couple to a one of at least three discrete segments of the LV cardiac tissue, and wherein said at least three discrete segments of LV cardiac tissue comprises: an apical portion, a mid-basal segment and an apical segment, along either an anterior, posterior or lateral plane; and an implantable pulse generator operatively coupled to a proximal portion of said elongated medical electrical lead, said implantable pulse generator further comprising:

means for sensing cardiac events, means for measuring intrathoracic impedance by injecting direct current signals using a one of the at least three individually addressable electrodes and calculating a resulting impedance value, means for delivering diverse electrical therapies, and means for optimizing cardiac pacing intervals by individually addressing at least a pair of said at least three individually addressable electrodes, and, as applicable, applying programmably-timed pacing-level electrical stimulation, wherein said switching means further comprises means for altering connections among said implantable pulse generator and said one or more of said at least three individually addressable electrodes to eliminate or reduce said inappropriate signal, and wherein said switching means comprises a modulator/demodulator units and further comprises: means for resuming stimulation and contraction of the cardiac tissue at the alternate segment via the individually addressable electrodes.

* * * * *

UNITED STATES PATENT AND TRADEMARK OFFICE
CERTIFICATE OF CORRECTION

PATENT NO. : 7,142,919 B2 Page 1 of 1
APPLICATION NO. : 10/692647
DATED : November 28, 2006
INVENTOR(S) : Hine et al.

It is certified that error appears in the above-identified patent and that said Letters Patent is hereby corrected as shown below:

Column 32, line 36 please change "comprise" to --comprises--.

Column 32, line 39 please change "comprises;" to --comprises:--.

Signed and Sealed this

Twenty-third Day of October, 2007

JON W. DUDAS
*Director of the United States Patent and Trademark Office*